United States Patent [19]

Fosker et al.

[11] 4,312,982
[45] Jan. 26, 1982

[54] α-ACYLUREIDOCEPHALOSPORINS AND SALTS AND ESTERS THEREOF

[75] Inventors: George R. Fosker, Horsham; George Burton, Coulsdon, both of England

[73] Assignee: Beecham Group Limited, England

[21] Appl. No.: 683,792

[22] Filed: May 6, 1976

Related U.S. Application Data

[63] Continuation of Ser. No. 478,741, Jun. 12, 1974, abandoned.

[30] Foreign Application Priority Data

Jun. 12, 1973 [GB] United Kingdom ............... 27970/73
Oct. 20, 1973 [GB] United Kingdom ............... 48968/73

[51] Int. Cl.³ ................. C07D 501/32; C07D 501/34; C07D 501/54; C07D 501/56
[52] U.S. Cl. ........................................ 542/418; 544/24; 544/25; 544/26; 544/27; 544/28; 544/29; 544/30; 424/246
[58] Field of Search .................. 542/418; 544/4, 16, 544/22, 23, 24, 25, 26, 27, 28, 29, 30

[56] References Cited

U.S. PATENT DOCUMENTS

| 3,673,183 | 6/1972 | Erickson | 544/30 X |
| 3,687,949 | 8/1972 | Holdrege | 544/25 |
| 3,741,962 | 6/1973 | Breuer | 544/25 |
| 3,925,368 | 12/1975 | Cooper et al. | 542/418 |
| 3,954,802 | 4/1976 | Kocis et al. | 544/24 X |
| 3,956,292 | 5/1976 | Cooper | 544/27 |
| 4,061,630 | 12/1977 | Herron | 544/16 |
| 4,086,340 | 4/1978 | Schröck et al. | 424/246 |
| 4,093,722 | 6/1978 | Schröck et al. | 424/246 |
| 4,107,304 | 8/1978 | Schröck et al. | 424/246 |
| 4,224,442 | 9/1980 | Cooper et al. | 544/27 |

Primary Examiner—Donald G. Daus
Assistant Examiner—Diana G. Rivers
Attorney, Agent, or Firm—Jacobs & Jacobs

[57] ABSTRACT

Compounds which are clinically important cephalosporins and salts and esters thereof having a wide spectrum of activity against Gram-positive bacteria but especially against Gram-negative bacteria such as Pseudomonas spp. against which commercially available cephalosporins are normally inactive. Preferred compounds of the invention are also active against Gram-negative cephalosporinase-producing organisms such as Enterobacter spp., Serratia spp. and indole-positive Proteus; methods of preparation are described.

13 Claims, No Drawings

α-ACYLUREIDOCEPHALOSPORINS AND SALTS AND ESTERS THEREOF

CROSS REFERENCE

This is a continuation of Ser. No. 478,741 filed June 12, 1974, and now abandoned.

This invention relates to cephalosporins which have, in general, a broad spectrum of antibacterial activity, being active against many species of Gram-positive and Gram-negative bacteria. They are, therefore, useful as therapeutic (and, to a lesser extent, prophylactic) agents in animals, including man and poultry. The invention further relates to methods for the preparation of these cephalosporins and to their use in therapy.

Although there are now available a number of semi-synthetic cephalosporins having what is known as broad spectrum activity, no single cephalosporin is yet available which has a clinically useful level of antibacterial activity against all the pathogenic organisms encountered in clinical practice The search thus continues for broad-spectrum cephalosporins which have advantages, either in improved antibacterial effectiveness or wider spectrum of activity over the available cephalosporins.

According to the present invention there is provided a cephalosporin of formula (I) or a pharmaceutically acceptable salt or ester thereof:

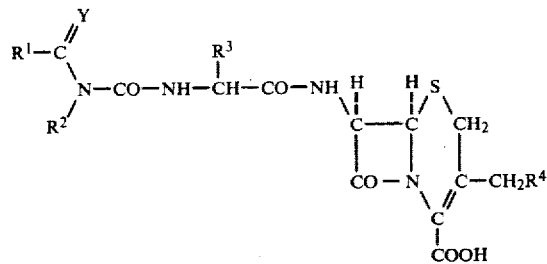

wherein Y is oxygen or sulphur, $R^1$ is an organic radical containing up to 20 carbon atoms; $R^2$ is alkyl having from 1 to 3 carbon atoms, or benzyl; or $R^1$ and $R^2$ together with the carbon and nitrogen atoms to which they are attached form a 5,6 or 7 membered ring; $R^3$ is phenyl, phenyl substituted by one or more functional groups selected from hydroxy, halogen, nitro, alkoxy containing from 1 to 3 carbon atoms, and amino groups, 2- or 3-thienyl, cycloalkyl having from 3 to 7 carbon atoms or alkyl having from 1 to 4 carbon atoms; $R^4$ is acetoxy or is a carbon, nitrogen or a sulphur nucleophile. Preferably Y is oxygen.

The group $R^1$ may for example be $C_{1-10}$ alkyl; $C_{1-10}$ alkenyl; aralkyl or aralkenyl in which the alkyl and alkenyl radicals are $C_{1-10}$ and the aryl radicals are phenyl, thienyl, furyl, pyridyl or substituted phenyl wherein the substituents are selected from $C_{1-13}$ alkyl, $C_{1-3}$ alkoxy, halogen, nitro and amino groups; $C_{1-10}$ alkoxy, $C_{5-7}$ cycloalkoxy; $C_{1-10}$ alkylamino; phenyl; furyl; thienyl; pyridyl; substituted phenyl wherein the substituents are selected from $C_{1-3}$ alkyl, $C_{1-3}$ alkoxy, halogen, nitro and amino groups; functionally substituted $C_{1-10}$ alkyl wherein the functional substituent is, for example, $C_{1-3}$ alkylthio, $C_{1-3}$ alkoxy or phenoxy.

Specifically, the group $R^1$ may be, for example, methyl, ethyl, n- or iso-propyl, n-; sec- or tert-butyl, n-pentyl, n-hexyl, n-heptyl, ω-methylheptyl, n-octyl, ω,ω-dimethyloctyl, prop-2-enyl, 3-methylprop-2-enyl, 1-methyl-prop-2-enyl, but-2-enyl, oct-2-enyl, 2-phenylethyl, 2-phenylethenyl, 2-(2¹-methoxyphenyl)ethenyl, 2-(4¹-nitrophenyl)ethen-yl,2-(3¹,4¹,5¹-trimethoxyphenyl)ethenyl, 2-(fur-2¹-yl)enyl. 3-phenylpropyl, 1-methyl-2-phenylethenyl, 4-phenylbut-2-enyl, 5-phenylpent-2-enyl, 1-methyl-5-phenylpent-2-enyl, methoxy, ethoxy, n- or sec-propoxy, n-, sec- or tert-butoxy, n-pentoxy, n-hexyloxy, cyclohexyloxy, methylamino, dimethylamino, phenyl, 2-methoxyphenyl, 2-chlorophenyl, 2-methoxy phenyl, 3,4,5-tri-methoxyphenyl, 4-nitrophenyl, 2-methylphenyl, 4-methylphenyl, methoxymethyl, ethoxymethyl, methylthiomethyl, phenoxymethyl.

The group $R^2$ may be, for example, methyl, ethyl or benzyl. Preferably $R^2$ is methyl.

When $R^2$ and $R^1$ are taken together with the carbon and nitrogen atoms to which they are joined, the ring which is formed may be, for example, one of the following:

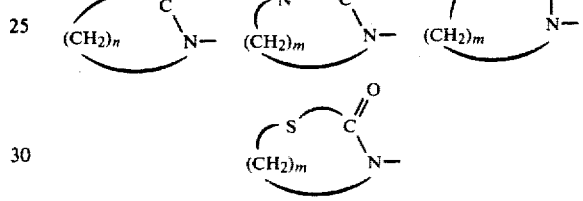

in which n is an integer from 3 to 5 and m is an integer from 2 to 4 and $R_a$ is hydrogen, $C_{1-3}$ alkyl, $C_{1-3}$ acyl or $C_{1-3}$ alkylsulphonyl. Preferably the ring formed is imidazolidin-2-on-1-yl, 3-acetylimidazoldin-2-on-1-yl, 3-methylsulphonyl-imidazolidin-2-on-1-yl or hexahydroazepin-2-on-1-yl.

The group $R^3$ may be, for example, phenyl, 4-hydroxyphenyl, 3-chloro-4-hydroxyphenyl, 4-nitrophenyl, 4-aminophenyl, 2-thienyl, 3-thienyl, cyclopropyl, cyclohexyl, cyclohexa-1,4-dienyl, iso -propyl or methyl group. Preferably $R^3$ is phenyl, 4-hydroxyphenyl, 3-chloro-4-hydroxyphenyl or 3-thienyl.

The group $R^4$ may be inter alia a strong carbon, nitrogen or sulphur nucleophile. Such nucleophiles displace the acetoxy group from the nucleus of 7-aminocephalosporanic acid and such displacement has been observed with various pyridines (Hale et.al. Biochem J. 79, 403, (1961) and Spencer et.al., J.Org. Chem (U.S.A.) 32 500, (1967)); other aromatic heterocycles (Hale et.al loc.cit;) Kariyone et al J. Antibiotics, 23, 131 (1970); and Spencer et.al. loc. cit.); Xanthates and dithiocarbromates Van Heyningen et.al. J.Chem.Soc. (London) 5015 (1965)) and anilines Bradshaw et.al. J.Chem.Soc. (London) 801 (1968)). Examples of particular $R^4$ groups include the following:

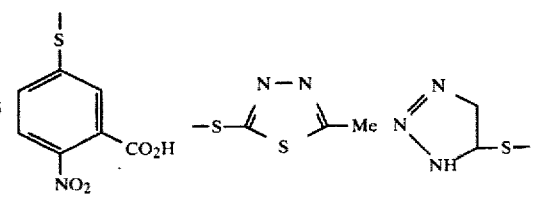

-continued (A = H or —CH₂CO₂H)

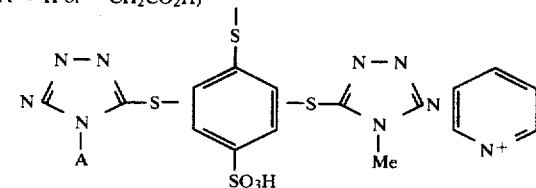

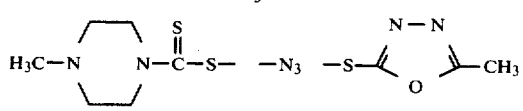

(B = O,S)

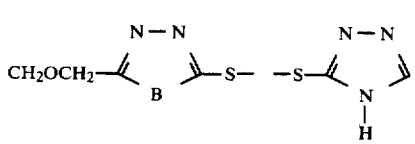

Preferably R⁴ is 2-methyl-1,3,4-thiadiazolyl-5-thio, 1-methyl-(1H)-1,2,3-tetrazolyl-5-thio, 2-methyl-1,3,4-oxadiazolyl-5-thio or (1H)-1,2,4-triazolyl-5-thio.

Preferably the configuration of the carbon atom to which the group R³ is attached is D.

Suitable pharmaceutically acceptable salts include the sodium, potassium, calcium, magnesium or aluminium salts and ammonium or substituted ammonium salts, e.g. those with trialkylamines such as triethylamine, procaine, dibenzylamine and triethanolamine.

In the case of compounds (I) which contain a basic nitrogen site in the side chain, acid addition salts may also be formed. Such salts include, for example, inorganic salts such as the sulphate, nitrate, phosphate, borate and hydrohalides e.g. hydrochloride, hydrobromide and hydroiodide, and organic salts such as the acetate, oxalate, tartrate, malate, citrate, succinate, benzoate, ascorbate and methanesulphonate.

Suitable pharmaceutically acceptable esters include especially those which break down readily in the human body to leave the parent acid e.g. acyloxyalkyl esters such as acetoxymethyl, pivaloyloxymethyl, α-acetoxyethyl, α-acetoxybenzyl and α-pivaloyloxymethyl, and alkoxycarbonylalkyl esters such as methoxycarbonyloxymethyl or α-methoxycarbonyloxyethyl esters. Other suitable esters of the readily hydrolysable type include lactone, thiolactone and dithiolactone esters (i.e. compounds of formula (I) wherein the 4-carboxy group is esterified as

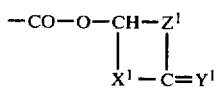

wherein X¹ and Y¹ are oxygen or sulphur and Z¹ is a divalent radical) especially the phthalide and substituted phthalide esters e.g. 5,6-dimethoxyphthalide esters.

The compounds of formula (I), it will be noted, fall into two structural classes, namely those wherein the group R¹ is joined to the carbonyl group via a C—C bond and those wherein it is joined via an N—C bond.

The compounds of this invention may be prepared by reacting a compound of formula (II) or a salt, ester or silyl derivative thereof:

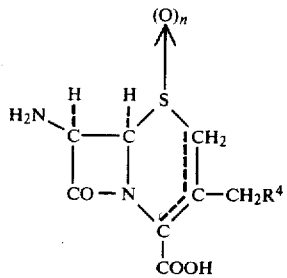

wherein the dotted line represents a bond in the 2- or 3-position, n is 0 or 1 and R⁴ is as defined with respect to formula (I) with a reactive N-acylating derivative of an acid of formula (III):

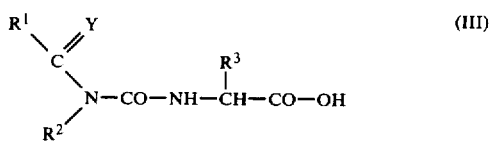

wherein Y, R¹, R² and R³ are as defined in formula (I) and wherein any reaction groups, such as amino and hydroxy groups may be blocked, and thereafter, if necessary carrying out one or more of the following steps:

(i) converting a Δ² isomer into the desired Δ³ isomer
(ii) removal of any silyl groups by alcoholysis or hydrolysis (iii) reduction of a sulphoxide compound to form the desired sulphide compound (iv) removal of any blocking groups in the acyl side chain R (v) conversion of an ester compound to a free acid compound or salt thereof.

By the term "silyl derivative" of compound (II) we mean the product of the reaction between compound (II) and a silylating agent such as a halodialkylsilane, a halotrialkylsilane, a halodialkoxysilane or a halotrialkoxysilane, or a corresponding aryl or aralkylsilane and compounds such as hexamethyldisilazane. The silyl derivatives of compound (II) are extremely sensitive to moisture and hydroxylic compounds, and, after, reaction with the N-acylating derivatives of the acid (II), the silyl groups of the intermediate acylated compound can be removed by alcoholysis or hydrolysis.

A reactive N-acylating derivative of the acid (II) is employed in the above process. The choice of reactive derivative will of course be influenced by the chemical nature of the substituents in the acid. Thus, when the acid contains only acid stable groups, an acid halide is a suitable N-acylating derivative, preferably the acid chloride.

Such reagents, would however, be avoided when an acid labile group was present in the acid (III). In such cases a suitable N-acylating derivative is a mixed anhydride. For this purpose particularly convenient mixed anhydrides are the alkoxyformic anhydrides.

Alternative N-acylating derivatives of acid (III), are activated esters. Such activated esters, for example the ester formed with 1-hydroxybenzotriazole or N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (II) include the reactive intermediate formed by reaction in situ with a carbodiimide or carbonyldiimidazole, but the literature on the preparation of semi-synthetic penicillins contains examples of other reactive N-acylating derivatives of acids suitable for coupling to 6-APA.

It will be understood, of course, that where a free acid of type (I) or a salt thereof is desired, it may be convenient to carry out the acylation reaction using an ester of (II), and then to remove the ester group. Vice versa, if an ester is required, it may be convenient to carry out the acylation reaction using 7-ACA or a salt thereof and thereafter to esterify the free acid.

In the above process, if it is necessary to block any reactive substituents in the acid (III), conventional chemical blocking groups are known. Thus, if desired, any free amino groups may be blocked by conversion to t-butyloxycarbonyl or benzyloxycarbonylamino groups, or the amino group may be blocked as the nitro group which is later converted to the amino group.

When the compound resulting after N-acylation contains a sulphoxide group at the 1-position of the cephem ring this may be reduced by conventional methods, for example, those described in British Pat. No. 1,280,693. One such method is treatment with triphenylphosphine and acetyl chloride. When the resultant compound is a $\Delta^2$ cephem, the desired $\Delta^3$ cephem may be obtained by treatment of the former with a base, e.g. an alkali metal hydroxide or tertiary amine bases such as pyridine and triethylamine, or by oxidation to the $\Delta^2$ cephem sulphoxide followed by reduction to the $\Delta^3$ cephem. Methods for converting an ester compound to a free acid or base will depend on the particular ester in question, for example acid—or base—hydrolysis as well as enzymically catalysed hyrolysis may be used. However, to minimise isomerisation and side reactions aqueous solvents are better avoided and Lewis acids are preferable as means for de-esterification in appropriate cases.

Another method for the preparation of compound (I) is to react a compound of formula (IV) or a salt ester or silyl derivative thereof:

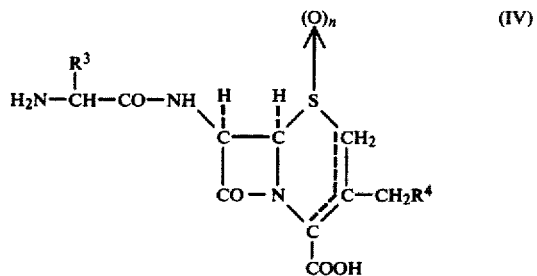

wherein the dotted line represents a bond in the 2- or 3-position, $R^3$ and $R^4$ are as defined with respect to formula (I), with a compound of formula (V)

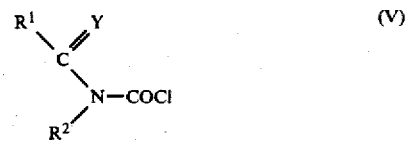

wherein Y, $R^1$, $R^2$ and $R^3$ are as defined with respect to formula (I), and, thereafter, if necessary, carrying out one or more of the following steps:

(i) converting a $\Delta^2$ isomer into the desired $\Delta^3$ isomer (ii) removal of any silyl groups by alcoholysis or hydrolysis (iii) reduction of a sulphoxide compound to form the desired sulphide compound (iv) removal of any blocking groups in the acyl side chain R (v) conversion of an ester compound to a free acid compound or salt thereof.

The compounds of this invention wherein $R^4$ is a carbon, sulphur or nitrogen nucleophile, may also be prepared from the corresponding compound wherein $R^4$ is acetoxy, by nucleophilic displacement of the acetoxy group. In such a process, a compound of formula (VI) or a salt, ester or silyl derivative thereof:

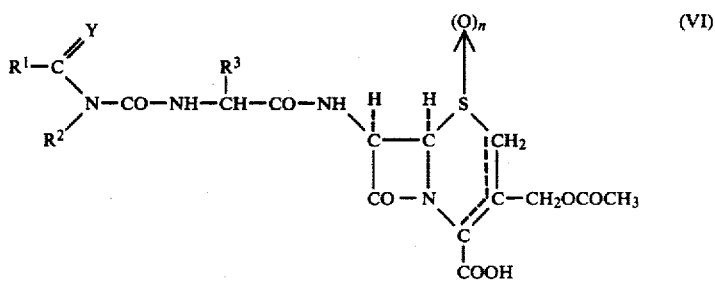

wherein the dotted line represents a bond in the 2- or 3-position, n is 0 or 1, Y, $R^1$, $R^2$, and $R^3$ are as defined in formula (I), and wherein any reactive groups may be blocked, is reacted with the appropriate carbon, nitrogen or sulphur nucleophile and thereafter, if necessary, one or more of the following steps is carried out:

(i) converting a $\Delta^2$ isomer into the desired $\Delta^3$ isomer (ii) removal of any silyl groups by alcoholysis or hydrolysis (iii) reduction of a sulphoxide compound to form the desired sulphide compound (iv) removal of any blocking groups in the acyl side chain R (v) conversion of an ester compound to a free acid compound or salt thereof.

The compounds of this invention are broad spectrum cephalosporins, i.e. cephalosporins which not only have activity against Gram-positive bacteria, but also against a number of clinically important Gram-negative organisms. The preferred compounds of this invention are active against such important organisms as Pseudomonas spp. against which the commercially available cephelosporins are normally inactive. In addition the preferred compounds are active against a number of Gram-negative cephalosporinase producing organisms e.g. Enterobacter spp. Serratia spp, indole-positive Proteus.

The following Examples illustrate the preparation of some of the compounds of this invention.

EXAMPLE 1

Preparation of Sodium
D-α-(N-imidazolidin-2-onylecarbonylamino) benzyl cephalosporin D-α-amino benzyl cephalosporin dihydrate (2.2 g) was dissolved in water (30 ml), acetone (5 ml) and triethylamine (0.7 ml). A solution of imidazolidin-2-onyl carbonyl chloride (0.75 g) in dry acetone (20 ml) was slowly added together with a further equivalent of triethylamine (0.7 ml) at such a rate to hold the pH of the reaction mixture at between 7.5 and 8.0. After the addition was complete, (about 5 minutes), the mixture was stirred for 1 hour with little further change in pH. The acetone was then removed under reduced pressure, the aqueous concentrate covered with ethyl acetate (35 ml) and the two phases chilled to 0° C. The pH was carefully adjusted to 1.5 with dilute hydrochloric acid with vigorous stirring. The phases were separated and the aqueous phase quickly re-extracted with fresh ethyl acetate (15 ml). The combined organic phases were washed with water (20 ml) and then with saturated brine solution (2×50 ml). The organic phase was then filtered through a siliconised filter paper to remove the final traces of brine solution and then treated with 1.0 N sodium 2-ethylhexoate/isopropanol (5 ml) with stirring. The pale yellow precipitate was filtered, thoroughly washed with dry diethyl ether and finally dried in vacuo to give the required cephalosporin, [(1.2 g), i.r. $\nu$max. (nujol) 1768 cm$^{-1}$ (β-lactam CO)]. This material gave an iodometric assay of 54%, and when subjected to paper chromatography in butanol-ethanol-water, had an $R_f$ 0.23, whereas the starting material, cephaloglycin, exhibited an $R_f$ of 0.19.

EXAMPLE 2

Preparation of Sodium D-α-(N-3-cinnamoyl-3-methyl ureido) benzyl cephalosporin

A solution of D-α-aminobenzyl cephalosporin (2.2 g) in water (30 ml), acetone (5 ml) and triethylamine (0.7 ml) was treated with N-chloroformyl-N-methyl cinnamide (1.12 g) in dry acetone (25 ml), simultaneously with a further equivalent of triethylamine (0.7 ml), such that the pH of the reaction mixture was maintained at 7.5 to 8.0. Upon completion of the addition, (about 5–8 minutes), the reaction mixture was stirred for 1 hour further when the acetone was removed by two thorough diethylether (2×100 ml) extractions. The pale yellow aqueous phase was covered with ethyl acetate (40 ml), chilled to 0° C. and carefully acidified to 1.5 with dilute hydrochloric acid with continuous, vigorous stirring. The phases were separated, the aqueous phase re-extracted with fresh ethyl acetate (20 ml). The combined organic phases were washed with water (20 ml) followed by saturated brine solution (2×50 ml). The last traces of brine were removed by filtration through a silicone-filter paper and then treated with 1.0 N sodium 2-ethyl hexoate/isopropanol (5 ml) with stirring. The thick white precipitate was filtered, well washed with dry diethyl ethyl and finally dried in vacuo to yield the desired material [(2.8 g) i.r. $\nu$max. (nujol) 1770 cm$^{-1}$ (β-lactam CO)]. When subjected to paper chromatography (butanol-ethanol-water), the product exhibited an $R_f$ of 0.51 and gave an iodometric assay of 58%.

EXAMPLE 3

Sodium D-α-(3-Ethoxycarbonyl-3-methylureido)benzyl cephalosporin

D-α-Aminobenzylcephalosporin dihydrate (2.2 g.) and triethylamine (1.5 ml.) in anhydrous dichloromethane (30 ml.) were stirred with molecular sieves, type 4A (2.0 g.), for two hours. The mixture was filtered, cooled in an ice bath and treated with ethyl N-chloroformyl N-methylcarbonate (0.84 g.) in dichloromethane (15 ml.). The solution was stirred at room temperature for two hours and evaporated to dryness in vacuo. The residue was dissolved in water (100 ml.) washed with ethylacetate (2×50 ml.) covered with ethylacetate (50 ml.) and acidified to pH 1.5 with N hydrochloric acid then filtered to remove insoluble material. The ethyl acetate was separated and the aqueous layer reextracted with water (2×50 ml) and saturated brine (50 ml.) dried over anhydrous magnesium sulphate, diluted with anhydrous ether (100 ml). and treated with 2 N sodium 2-ethylhexoate in methyl isobutylketone until precipitation ceased. The cephalosporin sodium salt was collected, washed with anhydrous ether and dried in vacuo over phosphorus pentoxide. Yield 1.25 g., 43.1%, n.m.r. spectrum [(CD$_3$)$_2$SO+D$_2$O]. δ=7.55 (5H, s, aromatic protons). 5.9–5.6 (2H, m, α- and C$_7$ protons), 5.3–4.7 (3H, m, C$_6$ proton and —C$\underline{H}$$_2$OCOCH$_3$), 4.38 [2H, q (J=7H$_z$), NCO$_2$C$\underline{H}$$_2$CH$_3$], 2.13 (3H, S, —OCOC$\underline{H}$$_3$), 1.41 [3H, t(J=7H$_z$) —CO$_2$CH$_2$C$\underline{H}$$_3$]. Paper chromatography in butanol-ethanol- water showed a single zone, $R_f$=0.49.

EXAMPLE 4

Sodium D-α(3-Cyclohexyloxycarbonyl-3-methylureido)benzyl cephalosporin

D-α-Aminobenzylcephalosporin dihydrate (2.2 g.) and cyclohexyl N-chloroformyl N-methylcarbonate (1.1 g.) were reacted together using the method described in example 3 to give the cephalosporin sodium salt, 1.01 g. 32%. N.m.r. spectrum [(CD$_3$)$_2$SO+D$_2$O], δ=7.40 (5H, s, aromatic protons), 5.8–5.4 (2H, m, C$_7$ and α-protons), 5.3–4.5 (4H, m, C$_6$ proton, —C$\underline{H}$$_2$OCOCH$_3$ and cyclohexylmethine proton), 3.5–3.0 (2H, m, C$_2$ protons), 3.10 (3H, s, >N—CH$_3$), 2.01 (3H, s, —OCOCH$_3$), 3.1–1.2 (10H, m, cyclohexylmethlene protons). Paper chromatography in butanol-ethanol-water showed one spot, $R_f$=0.60.

EXAMPLE 5

Sodium D-α(2,4-dimethylallophanamido)benzyl cephalosporin

Anhydrous triethylammonium D-α-aminobenzyl cephalosporinate (0.005 M) in dichloromethane (30 ml.) [prepared from the dihydrate of D-α-aminobenzyl cephalosporin (2.2 g.) as in example 3] was cooled in an ice bath and then 2,4-dimethylallophanoyl chloride (0.75 g.) in dichloromethane (15 ml.) was added. The solution was stirred at R.T. for two hours then evaporated to dryness in vacuo. The residue was dissolved in water (100 ml.), washed with ethyl acetate (2×50 ml.), covered with fresh ethyl acetate (50 ml.) and acidified to pH 1.5 with 1 N hydrochloric acid. The mixture was filtered to remove the insoluble material, the ethylacetate separated and the aqueous layer extracted with ethyl acetate (50 ml.). The combined ethyl acetate solutions were washed with water (2×50ml.) and saturated brine (50 ml.) then dried over anhydrous magnesium sulphate. After the magnesium sulphate had been filtered off, the ethyl acetate solution was reduced to ca. 25 ml. in vacuo and 2 N sodium 2-ethylhexoate in methyl isobutyl ketone (1.5 ml.) added. The precipitated sodium salt was collected and washed with anhydrous ether then dried in vacuo over phosphorus pentoxide. Yield · 1.29 g., 49.2%; n.m.r. spectrum [(CD$_3$)$_2$SO+D$_2$O], $\delta$=7.38 (5H,s, aromatic protons), 5.9–5.3 (2H, m, C$_7$ and $\alpha$-protons), 5.2–4.6 (4H,m, C$_6$ proton and —CH$_2$OCOCH$_3$), 3.5–2.9 (2H,m, C$_2$ methylene protons), 3.13 (3H,s, >N—CH$_3$), 2.73 (3H,s, —NHCH$_3$), 2.01 (3H,s, —OCOCH$_3$); u.v. spectrum (95% ethanol), $\lambda_{max}$ 261.5 nm ($\epsilon$=7,276). Paper chromatography in n-butanol-ethanol-water showed a single zone, R$_f$=0.41.

The following Example 6–17 were prepared by the method described in Example 5.

EXAMPLE 6

Sodium D-$\alpha$-(hexahydroazepin-2-one-1-ylcarbonylamino)benzyl cephalosporin From 1-chlorocarbonylhexahydroazepin-2-one and D-$\alpha$-aminobenzyl cephalosporin dihydrate in 40.3% yield; n.m.r. spectrum [(CD$_3$)$_2$SO+D$_2$O], $\delta$=7.44 (5H,s, aromatic protons), 5.7–5.5 (2H,m, $\alpha$-proton and C$_7$ proton), 5.2–4.6 (4H,m, C$_6$ proton and —CH$_2$OCOCH$_3$), 4.1–3.8 (2H,m, hexahydroazepinone C$_3$ methylene), 3.5–2.1 (2H,m, C$_2$methylene), 3.0–2.6 (2H,m, hexahydroazepinone C$_7$ methylene), 2.01 (3H,s, —OCOCH$_3$), 1.9–1.4 (6H,m, hexahydroazepinone C$_4$, C$_5$ and C$_6$ methylene protons); u.v. spectrum (95% ethanol), $\lambda_{max}$ 263.5 nm ($\epsilon$=6,509). Paper chromatography showed one zone R$_f$=0.58.

EXAMPLE 7

Sodium D-$\alpha$-(3-cinnamoyl-3-methylureido)benzyl cephalosporinate

From N-chlorocarbonyl-N-methylcinnamamide and D-$\alpha$-aminobenzyl cephalosporin dihydrate in 37.5% yield; n.m.r. spectrum [(CD$_3$)$_2$SO+D$_2$O], $\delta$=8.0–7.1 (12H,m, aromatic and definic protons), 5.8–5.5 (2H,m, C$_7$ and $\alpha$-protons), 5.3–4.6 (3H,m, C$_6$ and —CH$_2$OCO— protons), 3.35 (5H, singlet covering a multiplet, C$_2$ methylene and >N—CH$_3$), 2.04 (3H,s, —OCOCH$_3$); u.v. spectrum (95% ethanol), $\lambda_{max}$ 279 nm ($\epsilon$=18,326). Paper chromatography showed a zone at R$_f$=0.52.

EXAMPLE 8

Sodium D-$\alpha$-(3-crotonoyl-3-methylureido)benzyl cephalosporin

From N-chlorocarbonyl-N-methylcrotonamide and D-$\alpha$-amiobenzyl cephalosporin dihydrate in 24% yield; n.m.r. spectrum [(CD$_3$)$_2$SO+D$_2$O], $\delta$=1.89 (3H,m, =CHCH$_3$), 2.02 (3H,s, —OCO—CH$_3$), 3.23 (3H, singlet covering a multiplet, >N—CH$_3$ and C$_2$ methylene protons), 4.85-4.95 (3H,m, C$_6$ and —CH$_2$—OCOCH$_3$), 5.5–5.7 (2H,m, C$_7$ and $\alpha$-protons), 6.7–7.5 (2H,m, olefinic protons), 7.40 (5H,s, aromatic protons); u.v. spectrum (95% ethanol), $\lambda_{max}$ 265 nm ($\epsilon$=8,684). Paper chromatography showed a zone at R$_f$=0.48.

EXAMPLE 9

Sodium D-$\alpha$-(3-methyl-3-phenylpropionoylureido)benzyl cephalosporin

From N-chlorocarbonyl-N-methylphenylpropionamide and D-$\alpha$-aminobenzyl cephalosporin dihydrate in 55.5% yield; n.m.r. spectrum [(CD$_3$)$_2$SO+D$_2$O], $\delta$=1.03 (3H,s, —OCOCH$_3$), 2.8–3.5 (9H,m, <N—CH$_3$, —OCH$_2$CH$_2$— and C$_2$ methylene protons), 4.8–5.0 (3H,m, C$_6$ proton and —CH$_2$OCO—), 5.5–5.7 (2H,m, C$_7$ and $\alpha$-protons), 7.30 (5H,s, aromatic protons), 7.40 (5H,s, aromatic protons); u.v. spectrum (95% ethanol), $\lambda_{max}$ 264 nm ($\epsilon$=7,300). Paper chromatography showed a zone at R$_f$=0.63.

EXAMPLE 10

Sodium D-$\alpha$-[3-methyl-3-(o-methoxycinnamoyl)ureido]benzyl cephalosporin From N-chlorocarbonyl-N-methyl-o-methoxycinnamamide and D-$\alpha$-aminobenzyl cephalosporin dihydrate in 34.3% yield; n.m.r. spectrum [(CD$_3$)$_2$SO+D$_2$O], $\delta$=2.03 (3H,s, —OCOCH$_3$), 3.36 (3H,s, —OCH$_3$), 3.75 (5H, singlet covering a multiplet, >N—CH$_3$ and C$_2$ methylene), 4.85–5.05 (3H,m, C$_6$ proton and —CH$_2$OCO—), 5.60–5.80 (2H,m, C$_7$ and $\alpha$-protons), 7.0–8.2 (11H,m, olefinic and aromatic protons; u.v. spectrum (95% ethanol), $\lambda_{max}$ 229 ($\epsilon$=17,856), 277 ($\epsilon$=17,767) and 331 nm ($\epsilon$=11,249). Paper chromatography showed a zone at R$_f$=0.38.

EXAMPLE 11

Sodium D-$\alpha$-[3-methyl-3-(2'-thienyl)acryloylureido]benzyl cephalosporin From N-chlorocarbonyl-N-methyl-(2-thienyl)acrylamide and D-$\alpha$-aminobenzyl cephalosporin dihydrate in 26.3% yield; n.m.r. spectrum [(CD$_3$)$_2$SO+D$_2$O], $\delta$=2.03 (3H,s, —OCOCH$_3$), 3.32 (5,m, >N—CH$_3$ and C$_2$ methylene protons), 4.7–5.1 (2H,m, C$_6$ proton and —CH$_2$OCO—), 5.5–5.8 (2H,m, C$_7$ and $\alpha$-protons), 6.8–8.1 (10H,m, olefinic and aromatic protons); u.v. spetrum (95% ethanol), $\lambda_{max}$ 267 ($\epsilon$=12,843) and 322.5 nm ($\epsilon$=15,205). Paper chromatography showed a zone at R$_f$=0.63.

EXAMPLE 12

Sodium D-$\alpha$-[3-methyl-3-(p-nitrocinnamoyl)ureido]benzyl cephalosporin

From N-chlorocarbonyl-N-methyl-p-nitrocinnamamide and D-$\alpha$-aminobenzyl cephalosporin dihydrate in 13% yield; n.m.r. spectrum [(CD$_3$)$_2$SO+D$_2$O], $\delta$=1.97 (3H,s, —OCOCH$_3$), 2.74 (5H,m, >N-CH$_3$ and C$_2$ methylene protons), 4.7–5.2 (3H,m, —CH$_2$OCO— and C$_6$ proton), 5.5–6.0 (2H,m, C$_7$ and $\alpha$-protons), 7.0–8.3 (11H,m, aromatic and olefinic protons); u.v. spectrum (95% ethanol), $\lambda_{max}$ 266 nm ($\epsilon$=13,797). Paper chromatography showed a zone at R$_f$=0.57.

EXAMPLE 13

Sodium D-α-[3-methyl-3-(α-methylcinnamoyl)ureido]benzyl cephalosporin

From N-chlorocarbonyl-N-methyl-α-methylcinnamamide and D-α-aminobenzyl cephalosporin dihydrate in 33.5% yield; n.m.r. spectrum [(CD$_3$)$_2$SO+D$_2$O], δ=2.03 (3H,s, —OCOC$\underline{H}$$_3$), 2.10 (3H,d, C$\underline{H}$$_3$—CH=), 3.23 (3H,s, >N—C$\underline{H}$$_3$), 3.2–3.5 (2H,m, C$_2$ methylene), 4.8–5.0 (3H,m, —C$\underline{H}$$_2$OCO— and C$_6$ proton), 5.5–5.7 (2H,m, C$_7$ and α-protons), 6.80 (1H,m, >C=C$\underline{H}$—), 7.3–8.1 (10H,m, aromatic protons); u.v. spectrum λ$_{max}$ 266nm (ε=13,797). Paper chromatography showed a zone at R$_f$=0.67.

EXAMPLE 14

Sodium D-α-(3-benzyl-3-cinnamoylureido)benzyl cephalosporin

From N-chlorocarbonyl-N-benzylcinnamamide and D-α-aminobenzyl cephalosporin dihydrate in 49.5% yield; n.m.r. [(CD$_3$)$_2$SO+D$_2$O], δ=2.03 (3H,s, C$\underline{H}$$_3$OCO—), 3.33 (2H,m, C$_2$ methylene protons), 4.95 (3H,m, —C$\underline{H}$$_2$OCO— and C$_6$ proton), 5.28 (2H,m, PhC$\underline{H}$$_2$—), 5.67 (1H,d, C$_7$ proton), 5.72 (1H,s, α-proton), 7.40 (17H,m, aromatic and olefinic protons); u.v. spectrum (95% ethanol), λ$_{max}$ 289 nm (ε=14,100). Paper chromatography showed a zone at R$_f$=0.64.

EXAMPLE 15

Sodium D-α-[3-(3',4',5'-trimethoxybenzoyl)3-methylureido]benzyl cephalosporin From N-chlorocarbonyl-N-methyl-3,4,5-trimethoxybenzamide and D-α-aminobenzyl cephalosporin dihydrate in 27% yield; n.m.r. [(CD$_3$)$_2$SO+D$_2$O], δ=2.03 (3H,s, C$\underline{H}$$_3$OCO—), 3.17 (5H,m, >N—C$\underline{H}$$_3$ and C$_2$ methylene), 3.83 (9H,m, 3×C$\underline{H}$$_3$O—), 4.96 (3H,m, —CH$_2$OCO— and C$_6$ proton), 5.63 (1H,d, C$_7$ proton), 5.68 (1H,s, α-proton), 6.88 (2H,s, trisubstituted phenyl protons), 7.40 (5H,s, Ph—); u.v. spectrum (95% ethanol), λ$_{max}$ 265 nm (ε=11,832). Paper chromatography showed a zone at R$_f$=0.42.

EXAMPLE 16

Sodium D-α-[3-(ββ-dimethylacryloyl)-3-methylureido]benzyl cephalosporin

From N-chlorocarbonyl-N-methyl-ββ-dimethylacrylamide and D-α-aminobenzyl cephalosporin dihydrate in 24.7% yield; n.m.r. spectrum [(CD$_3$)$_2$SO+D$_2$O], δ=1.9–2.1

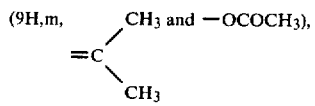

(9H,m, CH$_3$ and —OCOCH$_3$), 3.20 (2H, s, >N—CH$_3$), 3.2–3.4 (2H,m, C$_2$ methylene), 4.8–5.0 (3H,m, —C$\underline{H}$$_2$OCO— and C$_6$ proton), 5.6–5.8 (2H,m, C$_7$ and α-protons), 6.20 (1H,m, —C$\underline{H}$=C<), 7.42 (5H,s, aromatic protons); u.v. spectrum (95% ethanol), λ$_{max}$ 227 nm (ε=18,460). Paper chromatography showed a zone at R$_f$=0.62

EXAMPLE 17

Sodium D-α-[3-methyl-3-(3',4',5'-trimethoxycinnamoyl)ureido]benzyl cephalosporin From N-chlorocarbonyl-N-methyl-3,4,5-trimethoxycinnamamide and D-α-aminobenzyl cephalosporin dihydrate in 33.5% yield; n.m.r. spectrum [(CD$_3$)$_2$SO+D$_2$O], δ=2.03 (3H,s, —OCOC$\underline{H}$$_3$), 3.2–3.5 (2H,m, C$_2$ methylene), 3.36 (3H,s, >N—CH$_3$), 3.77 (3H,s, —OC$\underline{H}$$_3$), 3.87 (3H,s, —OC$\underline{H}$$_3$), 3.96 (3H,s, —OC$\underline{H}$$_3$), 4.8–5.0 (3H,m, C$_6$ and —C$\underline{H}$$_2$OCO—), 5.5–5.7 (2H,m, α-and C$_7$protons), 7.1–7.7 )9H,m, aromatic and olefinic protons); u.v. spectrum (95% ethanol), λ$_{max}$ 235.5 (ε=21,396) and 320 nm (ε=17,935). Paper chromatography showed a zone at R$_f$=0.63.

EXAMPLE 18

Sodium D-α-(2-imidazolidonecarbonylamino)benzyl cephalosporin

D-α-(21-Imidazolidonecarbonylamino)phenylacetic acid (1.32 g., 0.005 M) in anhydrous tetrahydrofuran (20 ml.) was cooled to <−10° and treated with N-methylmorpholine (1 drop), triethylamine (0.71 ml.) and ethyl chloroformate (0.48 ml.). The resulting suspension was stirred at <−10° for 15 mins. then an ice cooled solution of 7-aminocephalosporanic acid (1.36 g., 0.005 M) and triethylamine (0.71 ml.) in 50% aqueous tetrahydrofuran (30 ml.) was added. The solution was stirred at R.T. for three hours, tetrahydrofuran was then removed in vacuo and the residue dissolved in water (100 ml.) This aqueous solution was washed with ethyl acetate (2×50 ml.) and acidified to pH 1.5 with 1 N hydrochloric acid. The precipitate was collected and dried in vacuo, yield 0.87 g., then suspended in water (10 ml.) and 0.95 equivalents of 1 N sodium bicarbonate solution added. The solution was filtered and the filtrate evaporated to dryness in vacuo. Yield 0.70 g., 26%; n.m.r. [(CD$_3$)$_2$SO+D$_2$O], δ=9.17 [1H, d(J=8 Hz), —NH—], 7.41 (5H,s, aromatic protons), 5.9–5.4 (2H,m, C$_7$ and α-protons), 5.3–4.6 (3H,m, C$_6$ and —C$\underline{H}$$_2$OCO— protons), 4.1–3.1 (6H,m, C$_2$ methylene and imidazolidone methylenes), 2.01 (3H,s, —OCOCH$_3$); u.v. spectrum (95% ethanol) λ$_{max}$ 264 nm (ε=6,527). Paper chromatography in n-butanol, ethanol, water showed one zone, R$_f$=0.32.

EXAMPLE 19

Sodium D-α-(3-cinnamoyl-3-methylureido)benzyl cephalosporin

D-α-(3-Cinnamoyl-3-methylureido)phenylacetic acid (1.69 g., 0.005 M) in anhydrous acetone (15 ml.), was cooled to <−10° then N-methylmorpholine (1 drop), triethylamine (0.71 ml.) and ethyl chloroformate (0.48 ml.) were added. The resulting suspension was stirred at <−5° for 15 minutes then 7-aminocephalosporanic acid (1.36 g., 0.005 M) and triethylamine (0.71 ml.) in 50% aqueous acetone (30 ml.) pre-cooled to 0°, were added. The solution was stirred at R.T. for three hours, the acetone was removed in vacuo and the residue diluted with water (ca. 50 ml.). This aqueous solution was washed with ethyl acetate (2×50 ml.), covered with ethyl acetate (50 ml.), acidified to pH 1.5 with N-hydrochloric acid, the layers separated and the aqueous layer extracted with ethyl acetate (50 ml.). The combined organic solutions were washed with water (2×50 ml.)

and brine (50 ml.) then dried over anhydrous magnesium sulphate, concentrate in vacuo and treated with 2 N sodium 2-ethylhexoate in methyl isobutyl ketone (1.5 ml.). The precipitated solid was collected, washed with anhydrous ether and dried in vacuo. Yield 0.70 g., 22.8%; n.m.r. [(CD$_3$)$_2$SO+D$_2$O], δ=8.0–7.1 (12H,m, aromatic and olefinic protons), 5.8–5.4 (2H,m, C$_7$ and α-protons), 5.2–4.7 (3H,m, C$_6$ and —CH$_2$OCO— protons), 3.34 (5H, singlet covering a multiplet, >N—CH$_3$ and C$_2$ methylene), 2.05 (3H,s, —OCOCH$_3$); u.v. spectrum (95% ethanol), λ$_{max}$ 275 nm (ε=17,119). Paper chromatography showed a single zone, R$_f$=0.52.

EXAMPLE 20

Sodium D-α-(3-furylacryloyl-3-methylureido)benzyl cephalosporin

From D-α-(3-furylacryloyl-3-methylurieo)phenyl acetic acid and 7-aminocephalosporanic acid as in example 21 in 14% yield; n.m.r. spectrum [(CD$_3$)$_2$SO+D$_2$O], δ=2.03 (3H,s, —OCOCH$_3$), 3.32 (5H, singlet covering a multiplet, >N—CH$_3$ and C$_2$ methylene protons), 4.8–5.1 (3H,m, —CH$_2$OCO— and C$_6$ proton), 5.5–5.8 (2H,m, C$_7$ and α-protons), 6.6–7.9 (10H,m, furyl, olefinic and aromatic protons). Paper chromatography showed a zone at R$_f$=0.58.

EXAMPLE 21

Sodium D-α-(3-cinnamoyl-3'-methylureido)-4-hydroxybenzyl cephalosporin

From D-α-(3'-cinnamoyl-3'-methylureido)-4-hydroxyphenylacetic acid and 7-aminocephalosporanic acid by the method of example 21 in 35.9% yield; n.m.r. [(CD$_3$)$_2$SO+D$_2$O], δ=8.0–6.6 (11H,m, aromatic and olefinic protons), 5.8–5.4 (2H,m, C$_7$ and α-protons), 5.1–4.7 (3H,m, C$_6$ and —CH$_2$OCO—), 3.35 (5H,s, >N—CH$_3$ and C$_2$ methylene), 2.05 (3H,s, —OCOCH$_3$); u.v. spectrum (95% ethanol), λ$_{max}$ 225 (ε=24,468) and 282 nm (ε=19,152). Paper chromatography showed one zone, R$_f$=0.65.

EXAMPLE 22

Sodium 7-[D-α-(3'-cinnamoyl-3'-methylureido)-phenylacetamido]-3-(2''-methyl-1'',3'',4''-thiadiazol-5''-ylthio)methylceph-3-em-4-carboxylate D-α-(3-Cinnamoyl-3-methylureido)phenylacetic acid (0.85 g., 0.0025 M) in anhydrous acetone (10 ml.) was cooled to <−10° then N-methylmorpholine (1 drop), triethylamine (0.35 ml.) and ethyl chloroformate (0.24 ml.) were added. The resulting suspension was stirred at <−10° for 15 minutes then 7-amino-3-(2'-methyl-1',3',4'-thiadiazol-5'-ylthio)methylceph-3-em-4-carboxylic acid (0.86 g., 0.0025 M) and triethylamine (0.35 ml.) in 50% aqueous acetone (15 ml.) pre-cooled to 0° were added. The solution was stirred at R.T. for two hours, the acetone was removed in vacuo, the residue diluted with water (50 ml.) and washed with ethyl acetate (2×50 ml.). The aqueous layer was covered with ethyl acetate (50 ml.) and acidified to pH 1.5 with 1 N hydrochloric acid then the ethyl acetate layer was separated and the aqueous extracted with ethyl acetate (50 ml.). The combined ethyl acetate solutions were washed with water (2×50 ml.) and brine (50 ml.), dried over anhydrous magnesium sulphate and treated with 2 N sodium 2-ethylhexoate in methyl isobutyl ketone (0.7 ml.). The precipitated sodium salt was collected, washed with anhydrous either and dried in vacuo. Yield 0.53 g., 30.9%; n.m.r. [(CD$_3$)$_2$SO+D$_2$O], δ=8.0–7.0 (12H,m, aromatic and olefinic protons), 5.8–5.4 (2H,m, C$_7$ and α-protons), 5.1–4.8 (1H,m, C$_6$ proton), 4.8–4.0 (2H,m, —CH$_2$—S—), 3.34 (5H, singlet covering a multiplet, >N—CH$_3$ and C$_2$ methylene), 2.67 (3H,s, thiadiazole methyl protons); u.v. spectrum [95% ethanol]-λ$_{max}$ 219 (ε=24,010) and 282 nm (ε=27,901). Paper chromatography showed one zone, R$_f$=0.63.

EXAMPLE 23

Sodium 7-[D-α-(3'-cinnamoyl-3'-methylureido)-phenylacetamido]-3-(1''-methyl-1''H-tetrazol-5''-ylthio)methylceph-3-em-4-carboxylate N-Methylmorpholine (1 drop), triethylamine (0.35 ml.) and ethyl chloroformate (0.24 ml.) were added to D-α-(3-cinnamoyl-3-methylureido) phenylacetic acid (0.85 g., 0.0025 M) in anhydrous acetone (20 ml.) at <−10°, and stirred at that temperature for 15 minutes. 7-Amino-3-(1'-methyl-1'H-tetrazol-5'-ylthio)methylceph-3-em-4-carboxylic acid (0.82 g., 0.0025 M) and triethylamine (0.35 ml.) in 50% aqueous acetone (30 ml.) cooled to 0°, was added and the solution stirred at R.T. for two hours. Acetone was removed in vacuo and the residue diluted with water (100 ml.), washed with ethyl acetate (2×50 ml.), covered with ethyl acetate (50 ml.) and acidifed to pH 1.5 with 1 N hydrochloric acid. The layers were separated and the aqueous solution extracted with ethyl acetate (50 ml.). The combined extracts were washed with water (2×50 ml.). then dried over anhydrous magnesium sulphate and teated with 2 N sodium 2-ethylhexoate in methyl isobutyl ketone (0.8 ml.). The precipitated salt was collected, washed with anhydrous ether and dried in vacuo. Yield 0.64 g., 38.2%; n.m.r. [(CD$_3$)$_2$SO+D$_2$O]. δ=8.0–7.1 (12H,m, aromatic and olefinic protons), 5.8–5.5 (2H,m, C$_7$ and α-protons), 5.1–4.8 (1H,m, C$_6$ proton), 4.6–4.1 (2H,m, —CH$_2$—S—), 3.95 (3H,s, tetrazole methyl protons), 3.33 (5H, singlet covering a multiplet, >N—CH$_3$ and C$_2$ methylene protons); u.v. spectrum (95% ethanol), λ$_{max}$ 282 nm (ε=25,277). Paper chromatography showed one zone, R$_f$=0.66.

EXAMPLE 24

Sodium D-α-(3-benzoyl-3-methylureido)benzyl cephalosporin

Anhydrous triethylammonium D-α-aminobenzyl cephalosporin (0.005 M) in dichloromethane (30 ml) [prepared from D-α-amino-benzyl cephalosporin dihydrate (2.2 g) as in example 3] was cooled in an ice bath and then N-chlorocarbonyl-N-methylbenzamide (0.98 g., 0.005 M) in dichloromethane (15 ml) was added. The solution was stirred at R.T. for two hours then evaporated to dryness in vacuo. The residue was dissolved in water (100 ml), washed with ethyl acetate (2×50 ml) and acidified to pH 1.5 with 1 N hydrochloric acid in the presence of ethyl acetate (50 ml). The organic layer was separated off, the aqueous layer extracted with ethyl acetate (50 ml) and the combined ethyl acetate extracts were washed with water (2×100 ml) and saturated brine (50 ml) then dried over anhydrous magnesium sulphate. The dried solution was treated with 2 N sodium 2-ethylhexoate in methyl isobutyl ketone (1.5 ml), diluted with anhydrous ether (200 ml) and the precipitated sodium salt collected and dried in vacuo. Yield 1.68 g., 57.2%; N.M.R. spectrum

[(CD$_3$)$_2$SO+D$_2$O], δ=7.7–7.2 (10H,m, aromatic protons), 5.8–5.4 (2H,m, C$_7$ and α-protons), 5.2–4.6 (3H,m, C$_6$ proton and —CH$_2$OCO—), 3.6–2.8 (2H,m, C$_2$ methylene protons), 3.08 (3H,s, >NCH$_3$), 2.00 (3H,s, —OCOCH$_3$) U.V. spectrum (95% EtOH), λ$_{max}$ 263 nm (ε=8,710). Paper chromatography in n-butanol-ethanol-water showed one zone, R$_f$=0.52.

The following Examples 25–37 were prepared by the method described in example 24.

EXAMPLE 25

Sodium D-α-(3-methyl-3-acetylureido)benzyl cephalosporin

From N-chlorocarbonyl-N-methylacetamide and D-α-aminobenzyl cephalosporin dihydrate in 27.0% yield; N.M.R. spectrum [(CD$_3$)$_2$SO+D$_2$O], δ=7.43 (5H,s, aromatic protons), 6.8–6.5 (2H,m, C$_7$ and α-protons), 5.2–4.6 (3H,m, C$_6$ proton nd —CH$_2$OCO—), 3.7–2.7 (2H,m, C$_2$ methylene protons), 3.20 (3H,s, >NCH$_3$), 2.33 (3H,s, —COCH$_3$), 2.03 (3H,s, —OCOCH$_3$); U.V. spectrum (95% ethanol), λ$_{max}$ 266 nm (ε=7,920). Paper chromatography showed one zone, R$_f$=0.42.

EXAMPLE 26

Sodium D-α-[3-(2-methylcrotonoyl)-3-methylureido]benzyl cephalosporin

From N-chlorocarbonyl-N-methyl-2-methylcrotonamide and D-α-aminobenzyl cephalosporin dihydrate in 37.4% yield; N.M.R. spectrum [(CD$_3$)$_2$SO+D$_2$O], δ=1.5–2.2 (6H,m, =CHC$\underline{H}_3$ and —OCOCH$_3$), 3.12 (3H,s, >N—CH$_3$), 3.2–3.4 (2H,m, C$_2$ methylene protons), 4.9 (3H,m, C$_6$ proton and —CH$_2$OCO—), 5.6 (2H,m, C$_7$ and α-protons), 7.4 (5H,m, aromatic protons); U.V. spectrum (95% ethanol), λ$_{max}$ 257 nm (ε=7,930). Paper chromatography showed one zone, R$_f$=0.62

EXAMPLE 27

Sodium D-α-(3-phenylacetyl-3-methylureido)benzyl cephalosporin

From N-chlorocarbonyl-N-methylphenylacetamide and D-α-aminobenzyl cephalosporin dihydrate in 10.5% yield; N.M.R. spectrum [(CD$_3$)$_2$SO+D$_2$O], δ=2.03 (3H,s, —OCOC$\underline{H}_3$), 3.29 (5H,singlet covering a multiplet >NC$\underline{H}_3$ and C$_2$ methylene protons), 4.04 (2H,s, —COCH$_2$Ph), 4.92 (3H,m, —OCOCH$_2$— and C$_6$ proton), 5.7 (2H,m, C$_7$ and α-protons), 7.32, 7.40 (10H,d, aromatic protons); U.V. spectrum (95% ethanol), λ$_{max}$ 264 nm (ε=5,720). Paper chromatography showed a zone at R$_f$=0.51.

EXAMPLE 28

Sodium D-α-[3-(4-phenylbutanoyl)-3-methylureido]benzyl cephalosporin

From N-chlorocarbonyl-N-methyl-4-phenylbutyramide and D-α-aminobenzyl cephalosporin dihydrate in 49.2% yield; N.M.R. spectrum [(CD$_3$)$_2$S+D$_2$O], δ=2.02 (7H, singlet covering a multiplet, —OCOCH$_3$ and —CH$_2$CH$_2$Ph), 2.7 (2H,m, —COCH$_2$—), 3.18 (5H, singlet coverings multiplet, >NCH$_3$ and C$_2$ methylene protons), 4.92 (3H,m, —CH$_2$OCO— and C$_6$ proton), 5.65 (2H,m, C$_7$ and α-protons), 7.26 (5H,s, aromatic protons), 7.40 (5H,s, aromatic protons); U.V. spectrum (95% ethanol), λ$_{max}$ 261 nm (ε=7,785). Paper chromatography showed a zone at R$_f$=0.62.

EXAMPLE 29

Sodium D-α-(3-oct-2'-enoyl-3-methylureido)benzyl cephalosporin

From N-chlorocarbonyl-N-methyloct-2-enamide and D-α-aminobenzyl cephalosporin dihydrate in 25% yield; N.M.R. spectrum, [(CD$_3$)$_2$SO+D$_2$O], δ=0.8–1.5 (9H,m, —(CH$_2$)$_3$CH$_3$), 2.02 (5H, singlet covering a multiplet, —OCOCH$_3$ and —C$\underline{H}_2$CH=), 3.25 (5H, singlet covering a multiplet, >NCH$_3$ and C$_2$ methylene protons), 4.8–5.0 (3H,m, C$_6$ proton and —CH$_2$OCO—), 5.5–5.7 (2H,m, C$_7$ and α-protons), 6.5–7.5 (2H,m, olefinic protons), 7.42 (5H,s, aromatic protons). Paper chromatography showed a zone at R$_f$=0.58.

EXAMPLE 30

Sodium D-α-(3-furoyl-3-methylureido)benzyl cephalosporin

From N-chlorocarbonyl-N-methyl-2-furamide and D-α-aminobenzyl cephalosporin dihydrate in 55.0% yield; N.M.R. spectrum [(CD$_3$)$_2$S+D$_2$O], δ=2.04 (3H,s, —OCOCH$_3$), 3.37 (5H, singlet covering a multiplet, >NCH$_3$ and C$_2$ methylene protons), 4.8–5.0 (3H,m, —OCOCH$_2$— and C$_6$ proton), 5.5–5.8 (2H,m, C$_7$ and α-protons), 6.6–8.0 (8H,m, aromatic and furyl protons); U.V. spectrum (95% ethanol), λ$_{max}$ 268 nm (ε=19,990). Paper chromatography showed a zone at R$_f$=0.39.

EXAMPLE 31

Sodium D-α-(3-cinnamoyl-3-ethylureido)benzyl cephalosporin

From N-chlorocarbonyl-N-ethylcinnamamide and D-α-aminobenzyl cephalosporin dihydrate in 27.4% yield; N.M.R. spectrum [(CD$_3$)$_2$SO+D$_2$O], δ=1.2–1.4 (3H,m, C$\underline{H}_3$CH$_2$—), 2.04 (3H,s, —OCOCH$_3$), 3.2–3.5 (2H,m, C$_2$ methylene protons), 3.7–4.2 (2H,m, >N—CH$_2$—), 4.9–5.05 (3H,m, —OCOCH$_2$— and C$_6$ proton), 5.6–5.8 (2H,m, C$_7$ and α-protons), 7.3–8.0 (12H,m, aromatic and olefinic protons), U.V. spectrum (95% ethanol), λ$_{max}$ 285 nm (ε=19.370). Paper chromatography showed a zone at R$_f$=0.57.

EXAMPLE 32

Sodium D-α-(3-acetylimidazolin-2-on-1-ylcarbonylamino)benzyl cephalosporin

From D-α-aminobenzyl cephalosporin dihydrate and 3-acetyl-1-chlorocarbonylimidazolidin-2-one in 61.9% yield; N.M.R. spectrum [(CD$_3$)$_2$SO+D$_2$O], δ=7.42 (5H,s, aromatic protons), 5.8–5.3 (2H,m, C$_7$ and α-protons), 5.2–4.6 (3H,m, C$_6$ proton and —CH$_2$OCO—), 3.73 (4H,s, imidazolidone methylene protons), 3.6–2.9 (2H,m, C$_2$ methylene protons), 2.42 (3H,s, >NCOCH$_3$), 1.99 (3H,s, —OCOCH$_3$); U.V. spectrum (95% ethanol), λ$_{max}$ 260 nm (ε=8,180). Paper chromatography showed one zone R$_f$=0.30

EXAMPLE 33

Sodium D-α-(3-methylsulphonylimidazolidin-2-on-1-ylcarbonylamino)benzyl cephalosporin From D-α-aminobenzyl cephalosporin dihydrate and 1-chlorocarbonyl-3-methylsulphonylimidazolin-2-one in 38.1% yield; N.M.R. spectrum [(CD$_3$)$_2$S+D$_2$O], δ=7.48 (5H,s, aromatic protons), 5.7–5.4 (2H,m, C$_7$ and α-protons), 5.2–4.5 (3H,m, C$_6$ proton and —CH$_2$OCO—), 3.89 (4H,s, imidazolidinone methylene protons), 3.7–2.8 (2H,m, C$_2$ methylene protons), 3.38 (3H,s, —SO$_2$CH$_3$), 2.03 (3H,s, —OCOCH$_3$); U.V. spectrum (95% ethanol), λ$_{max}$ 262 nm (ε=7,825). Paper chromatography showed one zone, R$_f$=0.27.

EXAMPLE 34

Sodium D-α-(2,4,4-trimethylallaphanamido)benzyl cephalosporin

From 1-chlorocarbonyl-1,3,5-trimethylurea and D-α-aminobenzyl cephalosporin dihydrate in 33.2% yield; N.M.R. spectrum [(CD$_3$)$_2$SO+D$_2$O], δ=2.02 (3H,s, —OCOCH$_3$), 2.88 [6H,s, —N(CH$_3$)$_2$], 3.0 (3H,s, >NCH$_3$), 3.33 (2H,m, C$_2$ methylene protons), 4.93 (3H,m, C$_6$ proton and —CH$_2$OCO—), 5.58 (2H,m, C$_7$ and α-protons), 7.40 (5H,m, aromatic protons); U.V. spectrum (95% ethanol), λ$_{max}$ 266 nm (ε=6,890). Paper charomatography showed a zone at R$_f$=0.30.

EXAMPLE 35

Sodium D-α-(3-phenoxyacetyl-3-methylureido)benzyl cephalosporin

From N-chlorocarbonyl-N-methylphenoxyacetamide and D-α-aminobenzyl cephalosporin dihydrate in 62.1% yield; N.M.R. spectrum [(CD$_3$)$_2$SO+D$_2$O], δ=2.01 (3H,s, —OCOCH$_3$), 3.23 (5H, m, >NCH$_3$ and C$_2$ methylene protons), 4.92 (3H,m, —CH$_2$OCO— and C$_6$ proton) 5.10 (2H,s, PhOCH$_2$—), 5.61 (2H,m, C$_7$ and α-protons), 6.9 to 7.5 (10H,m, aromatic protons); U.V. spectrum (95% ethanol), λ$_{max}$ 266 nm (ε=9,000). Paper chromatography showed a zone at R$_f$=0.50

EXAMPLE 36

Sodium D-α-[3-(2-chlorobenzoyl)-3-methylureido]benzyl cephalosporin

From N-chlorocarbonyl-N-methyl-2-chlorobenzamide and D-α-aminobenzyl cephalosporin dihydrate in 28.5% yield; N.M.R. spectrum [(CD$_3$)$_2$SO=D$_2$O], δ=2.03 (3H,s, —OCOCH$_3$), 3.01 (3H,s, >N—CH$_3$), 3.2–3.5 (2H,m, C$_2$ methylene protons), 4.8–5.1 (3H,m, —CH$_2$OCO— and C$_6$ protons), 5.6–5.8 (2H,m, C$_7$ and α-protons), 7.3–7.7 (9H,m, aromatic protons); U.V. spectrum (95% ethanol), λ$_{max}$ 266 nm (ε=7,920), Paper chromatography showed a zone at R$_f$=0.58.

EXAMPLE 37

Sodium D-α-[3-(2-methylbenzoyl)-3-methylureido]benzyl cephalosporin

From N-chlorocarbonyl-N-methyl-2-methylbenzamide and D-α-aminobenzyl cephalosporin dihydrate in 51.5% yield; N.M.R. spectrum [(CD$_3$)$_2$SO+D$_2$O], δ=2.01 (3H,s, —OCOCH$_3$), 2.28 (3H,s, benzoyl —CH$_3$), 2.96 (3H,s, >N—CH$_3$), 3.2–3.4 (2H,m, C$_2$ methylene protons), 4.9–5.1 (3H,m, —CH$_2$OCO— and C$_6$ proton), 5.6–5.8 (2H,m, C$_7$ and α-protons), 7.3–7.5 (9H,m, aromatic protons); U.V. spectrum (95% ethanol), λ$_{max}$ 260 nm (ε=8,310). Paper chromatography showed a zone at R$_f$=0.50

EXAMPLE 38

Sodium 7-[D-α-(3-cinnamoyl-3-methylureido)-phenylacetamido]-3-(2-methyl-1,3,4-thiadiazol-5-ylthio)methylceph-3-em-4-carboxylate 7-(D-α-Aminophenylacetamido)-3-(2-methyl-1,3,4-thiadiazol-5-ylthio)methylceph-3-em-4-carboxylic acid trifluoroacetic acid (t.f.a.) salt (1.77 g., 0.003 M) and triethylamine (1.35 ml) in dichloromethane (30 ml) were cooled in an ice bath and treated with N-chlorocarbonyl-N-methylcinnamamide (0.78 g., 0.0035 M) in dichloromethane (10 ml). The solution was stirred at R.T. for three hours then evaporated to dryness in vacuo, the residue dissolved in water (50 ml) and washed with ethyl acetate (2×50 ml). The aqueous solution was covered with ethyl acetate (50 ml), acidified to pH 1.5 with 1 N hydrochloric acid, filtered, the ethyl acetate collected and the aqueous layer extracted with a further portion of ethyl acetate (50 ml). The combined extracts were washed with water (2×50 ml) and saturated brine (25 ml), dried over anhydrous magnesium sulphate and treated with 2 N sodium 2-ethylhexoate in methyl isobutyl ketone (1.0 ml). Anhydrous ether (200 ml) was added and the precipitated sodium salt collected and dried in vacuo. Yield 0.96 g., 46.6%; N.M.R. spectrum [(CD$_3$)$_2$SO+D$_2$O], δ=8.0–7.0 (12H,m, aromatic and olefinic protons), 5.8–5.5 (2H,m, C$_7$ and α-protons), 4.93 [1H,d,(J=5Hz), C$_6$-proton], 4.7–4.1 (2H,m, —CH$_2$S—), 3.8–2.9 (2H,m, C$_2$ methylene protons), 3.25 (3H,s, >NCH$_3$), 2.67 (3H,s, thiadiazole —CH$_3$); U.V. spectrum (95% ethanol), λ$_{max}$ 282 nm (ε=30,630). Paper chromatography showed one zone, R$_f$=0.65.

The following examples were prepared as described in example 38.

EXAMPLE 39

Sodium 7-[D-α-(3-cinnamoyl-3-methylureido)-phenylacetamido]-3-(1-methyl-1H-tetrazol-5-ylthio)methylceph-3-em-4-carboxylate From 7-(D-α-aminophenylacetamido)-3-(1-methyl-1H-tetrazol-5-ylthio) methylceph-3-em-4-carboxylic acid t.f.a. salt and N-chlorocarbonyl-N-methyl-cinnamamide in 50.7% yield; N.M.R. spectrum [(CD$_3$)$_2$SO+D$_2$O] δ=7.9–7.1 (12H,m, aromatic and olefinic protons), 5.8–5.5 (2H,m, C$_7$ and α-protons), 5.1–4.8 (1H,m, C$_6$ proton), 4.7–4.0 (2H,m, —CH$_2$S—), 3.93 (3H,s, tetrazole —CH$_3$), 3.8–3.1 (2H,m, C$_2$ methylene protons), 3.33 (3H,s, >NCH$_3$); U.V. spectrum (95% ethanol), λ$_{max}$ 282 nm (ε=24,490). Paper chromatography showed one zone, R$_f$=0.51.

EXAMPLE 40

Sodium 7-[D-α-(3-cinnamoyl-3-methylureido)-phenylacetamido]-3-(1H-1,2,4-triazol-3-ylthio)methylceph-3-em-4-carboxylate From 7-(D-α-aminophenylacetamido)-3-(1H-1,2,4-triazol-3-ylthio)methylceph-3-em-4-carboxylic acid t.f.a. salt and N-chlorocarbonyl-N-methylcinnamamide in 55.7% yield; N.M.R. [(CD$_3$)$_2$SO+D$_2$O], δ=8.0–7.0 (13H, aromatic, olefinic and triazole protons), 5.7–5.4 (2H,m, C$_7$ and α-protons), 5.0–4.3 (3H,m, C$_6$ proton and —CH$_2$S—), 3.8–3.0 (2H,m, C$_2$ methylene protons), 3.33 (3H,s, >N—CH$_3$); U.V. spectrum (95% ethanol), λ$_{max}$

EXAMPLE 41

Sodium 7-[D-α-(2,4-dimethylallophanamido)phenylacetamido]-3-(2-methyl-1,3,4-thiadiazol-5-ylthio)methylceph-3-em-4-carboxylate From 7-(D-α-aminophenylacetamido)-3-(2-methyl-1,3,4-thiadiazol-5-ylthio)methylceph-3-em-4-carboxylic acid t.f.a. salt and 2,4-dimethylallophanoyl chloride in 58.7% yield; N.M.R. spectrum [(CD$_3$)$_2$SO+D$_2$O], δ=7.7–7.1 (5H,m, aromatic protons), 5.7–5.5 (2H,m, C$_7$ and α-protons), 5.0–4.8 (1H,m, C$_6$ proton), 4.7–4.1 (2H,m, —CH$_2$S—), 3.10 (3H,s, >NCH$_3$), 2.70 (6H,s, —NHCH$_3$ and thiadiazole —CH$_3$); U.V. spectrum (95% ethanol), λ$_{max}$ 274 nm (ε=13,010). Paper chromatography showed one zone R$_f$=0.41.

EXAMPLE 42

Sodium 7-[D-α-(2,4-dimethylallophanamido)phenylacetamido]-3-(1-methyl-1H-tetrazol-5-ylthio)methylceph-3-em-4-carboxylate From 7-(D-α-aminophenylacetamido)-3-(1-methyl-1H-tetrazol-5-ylthio)methylceph-3-em-4-carboxylic acid t.f.a. salt and 2,4-dimethylallophanoyl chloride in 53.0% yield; N.M.R. spectrum [(CD$_3$)$_2$SO+D$_2$O], δ=7.42 (5H,s, aromatic protons), 5.7–5.5 (2H,m, C$_7$ and α-protons), 4.88 [1H,d, (J=5 Hz), C$_6$ proton], 4.6–4.0 (2H,m, —CH$_2$S—), 3.93 (3H,s, tetrazole —CH$_3$), 3.8–3.1 (2H,m, C$_2$ methylene protons), 3.10 (3H,s, >N—CH$_3$), 2.70 (3H,s, —NHCH$_3$); U.V. spectrum (95% ethanol), λ$_{max}$ 268 nm (ε=8,020). Paper chromatography showed one zone R$_f$=0.47.

EXAMPLE 43

Sodium 7-[D-α-(3-acetyl-methylureido)phenylacetamido]-3-(2-methyl-1,3,4-thiadiazol-5-ylthio)methylceph-3-em-4-carboxylate From 7-(D-α-aminophenylacetamido)-3-(2-methyl-1,3,4-thiadiazol-5-ylthio)methylceph-3-em-4-carboxylic acid t.f.a. salt and N-chlorocarbonyl-N-methylacetamide in 76.9% yield; N.M.R. spectrum [(CD$_3$)$_2$SO+D$_2$O], δ=7.47 (5H,s, aromatic protons), 5.8–5.4 (2H,m, C$_7$ and α-protons), 4.93 [1H,d, (J=5 Hz), C$_6$ proton], 4.7–4.0 (2H,m, —CH$_2$S—), 3.8–3.0 (2H,m, C$_2$ methylene protons), 3.21 (3H,s, >N—CH$_3$), 2.72 (3H,s, thiadiazole —CH$_3$), 2.33 (3H,s, —COCH$_3$); U.V. spectrum (95% ethanol), λ$_{max}$ 275 nm (ε=12,410). Paper chromatography showed one zone, R$_f$=0.31.

EXAMPLE 44

Sodium 7-[D-α-(3-acetyl-3-methylureido)phenylacetamido]-3-(1-methyl-1H-tetrazol-5-ylthio)methylceph-3-em-4-carboxylate From 7-(D-α-aminophenylacetamido)-3-(1-methyl-1H-tetrazol-5-ylthio)methylceph-3-em-4-carboxylic acid t.f.a. salt and N-chlorocarbonyl-N-methylacetamide in 24.8% yield; N.M.R. spectrum [(CD$_3$)$_2$SO+D$_2$O], δ=7.40 (5H,s, aromatic protons), 5.7–5.4 (2H,m, C$_7$ and α-protons), 4.89 [1H,d, (J=5 Hz), C$_6$ proton], 4.6–4.0 (2H,m, —CH$_2$S—), 3.94 (3H,s, tetrazole —CH$_3$), 3.8–3.1 (2H,m, C$_2$ methylene protons), 3.18 (3H,s, >N—CH$_3$), 2.30 (3H,s, —COCH$_3$); U.V. spectrum (95% ethanol), λ$_{max}$ 265 nm (ε=8,040). Paper chromatography showed one zone R$_f$=0.33.

EXAMPLE 45

Sodium 7-[D-α-[3-(4-phenylbutanoyl)-3-methylureido]-phenylacetamido]-3-(2-methyl-1,3,4-thiadiazol-5-ylthio)methylceph-3-em-4-carboxylate From N-chlorocarbonyl-N-methyl-4-phenylbutyramide and 7-(D-α-aminophenyl acetamido)-3-(2-methyl-1,3,4-thiadiazol-5-ylthio)methylceph-3-em-4-carboxylic acid t.f.a. salt in 46.8% yield; N.M.R. spectrum [(CD$_3$)$_2$SO+D$_2$O], δ=1.8–2.2 (2H,m, PhCH$_2$CH$_2$CH$_2$—), 2.5–2.9 (7H,m, thiadiazole —CH$_3$, —COCH$_2$CH$_2$CH$_2$Ph), 3.17 (3H,s, >N—CH$_3$), 3.3–3.5 (2H,m, C$_2$ methylene protons), 4.2–4.7 (2H,m, —CH$_2$S—), 4.8–5.0 (1H,m, C$_6$ proton), 4.5–4.8 (2H,m, C$_7$ and α-protons), 7.27 (5H,s, aromatic protons), 7.41 (5H,s, aromatic protons); U.V. spectrum (95% ethanol), λ$_{max}$ 275 nm (ε=12,770). Paper chromatography showed a zone at R$_f$=0.62.

EXAMPLE 46

Sodium 7-[D-α-[3-(4-phenylbutanoyl)-3-methylureido]-phenylacetamido]-3-(1-methyl-1H-tetrazol-5-ylthio)methylceph-3-em-4-carboxylate From N-chlorocarbonyl-N-methyl-4-phenylbutyramide and 7-(D-α-aminophenylacetamido)-3-(1-methyl-1H-tetrazol-5-ylthio)methylceph-3-em-4-carboxylic acid t.f.a. salt in 17.5% yield; N.M.R. spectrum [(CD$_3$)$_2$SO+D$_2$O], δ=1.7–2.2 (2H,m,PhCH$_2$CH$_2$CH$_2$—), 2.5–2.7 (4H,m, PhCH$_2$CH$_2$CH$_2$CO), 3.16 (3H,s, >N—CH$_3$), 3.4–3.6 (2H,m, C$_2$ methylene protons), 3.94 (3H,s, tetrazole —CH$_3$), 4.3–4.5 (2H,m, —CH$_2$—S—), 4.8–5.0 (1H,m, C$_6$ proton), 5.5–5.8 (2H,m, C$_7$ and α-protons), 7.25 (5H,s, aromatic protons), 7.37 (5H,s, aromatic protons); U.V. spectrum (95% ethanol), λ$_{max}$ 270 nm (ε=8,410). Paper chromatography showed a zone at R$_f$=0.47.

EXAMPLE 47

Sodium 7-[D-α-[3-(2-methylcrotonoyl)-3-methylureido]-phenylacetamido]-3-(1-methyl-1H-tetrazol-5-ylthio)methylceph-3-em-4-carboxylate From N-chlorocarbonyl-N-methyl-2-methyl crotonamide and 7-(D-α-aminophenylacetamido)-3-(1-methyl-1H-tetrazol-5-ylthio)methylceph-3-em-4-carboxylic acid t.f.a. salt in 17.1% yield, N.M.R. spectrum [(CD$_3$)$_2$SO+D$_2$O], δ=1.6–1.9 (6H,m, 2×crotonoyl —CH$_3$), 3.11 (3H,s, >N—CH$_3$), 3.4–3.6 (2H,m, C$_2$ methylene protons), 4.96 (3H,s, tetrazole —CH$_3$), 4.2–4.4 (2H,m, —CH$_2$S—), 4.7–5.1 (1H,m, C$_6$ proton), 5.5–6.0 (3H,m, —CH=C>, C$_7$ and α-protons), 7.40 (5H,s, aromatic protons), U.V. spectrum (95% ethanol), λ$_{max}$ 270 nm (ε=9,260). Paper chromatography showed a zone at R$_f$=0.43.

EXAMPLE 48

Sodium 7-[D-α-[3-(2-methylcrotonoyl)-3-methylureido]-phenylacetamido]-3-(2-methyl-1,3,4-thiadiazol-5-ylthio)methylceph-3-em-4-carboxylate From N-chlorocarbonyl-N-methyl-2-methyl crotonamide and 7-(D-α-aminophenylacetamido)-3-(2-methyl-1,3,4-thiadiazol-5-ylthio)methylceph-3-em-4-carboxylic acid t.f.a. salt in 35.6% yield; N.M.R. spectrum [(CD$_3$)$_2$SO+D$_2$O], δ=1.6–1.9 (6H,m, 2×crotonoyl —CH$_3$), 2.69 (3H,s, thiadiazole —CH$_3$), 3.12 (3H,s, >N—CH$_3$), 3.4–3.6 (2H,m, C$_2$ methylene protons), 4.3–4.6 (2H,m, —CH$_2$S—), 4.9–5.1 (1H,m, C$_6$ proton), 5.5–6.0 (3H,m, —CH=C>, C$_7$ and α-protons), 7.41 (5H,s, aromatic protons); U.V. spectrum (95% ethanol), λ$_{max}$ 275 nm (ε=13,470). Paper chromatography showed a zone at R$_f$=0.52.

EXAMPLE 49

Sodium 7-[D-α-[3-(3-phenylpropionyl)-3-methylureido]-phenylacetamido]-3-(2-methyl-1,3,4-thiadiazol-5-ylthio)methylceph-3-em-4-carboxylate From N-chlorocarbonyl-N-methyl-3-phenylpropionamide and 7-(D-α-aminophenylacetamido)-3-(2-methyl-1,3,4-thiadiazol-5-ylthio)methyl-ceph-3-em-4-carboxylic acid t.f.a. salt in 34.9% yield; N.M.R. spectrum [(CD$_3$)$_2$SO+D$_2$O], δ=2.68 (3H,s, thiadiazole —CH$_3$), 2.94 (4H,s, —CH$_2$CH$_2$Ph), 3.19 (3H,s, >N—CH$_3$), 3.3–3.5 (2H,m, C$_2$ methylene protons), 4.2–4.5 (2H,m, —CH$_2$S—), 4.8–5.0 (1H,m,C$_6$ proton), 5.4–5.7 (2H,m, C$_7$ and α-protons), 7.28 (5H,s, aromatic protons), 7.37 (5H,s, aromatic protons); U.V. spectrum (95% ethanol), λ$_{max}$ 275 nm (ε=13,500). Paper chromatography showed a zone at R$_f$=0.61.

EXAMPLE 50

Sodium 7-[D-α-[3-(3-phenylpropionyl)-3-methylureido]-phenylacetamido]-3-(1-methyl-1H-tetrazol-5-ylthio)methylceph-3-em-4-carboxylate From N-chlorocarbonyl-N-methyl-3-phenylpropionamide and (7-D-α-amino phenyl acetamido)-3-(1-methyl-1H-tetrazol-5-ylthio)methyl-ceph-3-em-4-carboxylic acid in t.f.a. salt 26.8% yield; N.M.R. spectrum [(CD$_3$)$_2$SO+D$_2$O], δ=2.94 (4H,s, —CH$_2$CH$_2$Ph), 3.19 (3H,s, >N—CH$_3$), 3.–3.8 (2H,m, C$_2$ methylene protons), 3.95 (3H,s, tetrazole —CH$_3$), 4.2–4.5 (2H, —CH$_2$S—), 4.8–5.0 (1H,m, C$_6$ proton), 5.5–5.8 (2H,m, C$_7$ and α-protons), 7.2–7.5 (10H,d, aromatic protons); U.V. spectrum (95% ethanol), λ$_{max}$ 260 nm (ε=9,120). Paper chromatography showed a zone at R$_f$=0.54.

EXAMPLE 51

Sodium 7-[D-α-[3-(3-methylcrotonoyl)-3-methylureido]-phenylacetamido]-3-(2-methyl-1,3,4-thiadiazol-5-ylthio)methylceph-3-em-4-carboxylate From N-chlorocarbonyl-N-methyl-3-methylcrotonamide and 7-(D-α-aminophenylacetamido)-3-(2-methyl-1,3,4-thiadiazol-5-ylthio)methylceph-3-em-4-carboxylic acid t.f.a. salt in 24.6% yield; N.M.R. spectrum [(CD$_3$)$_2$SO+D$_2$O], δ=1.9–2.1 (6H,m, —CH=C(CH$_3$)$_2$), 2.70 (thiadiazole —CH$_3$), 3.18 (3H,s, >N—CH$_3$), 3.3–3.6 (2H,m, C$_2$ methylene protons), 4.3–4.5 (2H,m, —CH$_2$S—), 4.8–5.0 (1H,m, C$_6$ proton), 5.5–5.7 (2H,m, C$_7$ and α-protons), 6.1–6.3 (1H,m, —CH=C<), 7.41 (5H,s, aromatic protons); U.V. spectrum (95% ethanol), λ$_{max}$ 270 nm (ε=11,870). Paper chromatography showed a zone at R$_f$=0.56.

EXAMPLE 52

Sodium 7-[D-α-[3-(3-methylcrotonoyl)-3-methylureido]-phenylacetamido]-3-(1-methyl-1H-tetrazol-5-ylthio)methylceph-3-em-4-carboxylate From N-chlorocarbonyl-N-methyl-3-methylcrotonamide and 7-(D-α-aminophenylacetamido)-3-(1-methyl-1H-tetrazol-5-ylthio)methylceph-3-em-4-carboxylic acid t.f.a. salt in 56.7% yield; N.M.R. spectrum [(CD$_3$)$_2$SO+D$_2$O], δ=1.9–2.1 (6H,m, —CH=C(CH$_3$)$_2$), 3.18 (3H,s, >N—CH$_3$), 3.4–3.6 (2H,m, C$_2$ methylene protons), 3.96 (3H,s, tetrazole —CH$_3$), 4.3–4.5 (2H,m, —CH$_2$S—), 4.9–5.0 (1H,m, C$_6$ proton), 5.5–5.8 (2H,m, C$_7$ and α-protons), 6.1–6.3 (1H,m, —CH=C<), 7.40 (5H,s, aromatic protons); U.V. spectrum (95% ethanol), λ$_{max}$ 274 nm (ε=10,130). Paper chromatography showed a zone at R$_f$=0.40.

EXAMPLE 53

Sodium 7-[D-α-(3-furoyl-3-methylureido)phenylacetamido]-3-(2-methyl-1,3,4-thiadiazol-5-ylthio)methylceph-3-em-4-carboxylate From N-chlorocarbonyl-N-methylfuramide and 7-(D-α-aminophenylacetamido)-3-(2-methyl-1,3,4-thiadiazol-5-ylthio)methylceph-3-em-4-carboxylic acid t.f.a. salt in 32.6% yield, N.M.R. spectrum [(CD$_3$)$_2$SO+D$_2$O], δ=2.69 (3H,s, thiadiazole —CH$_3$), 3.35 (5H,singlet covering multiplet, >N—CH$_3$ and C$_2$ methylene protons), 4.2–4.5 (2H,m, —CH$_2$S—), 4.9–5.1 (1H,m, C$_6$ proton), 5.5–5.8 (2H,m, C$_7$ and α-protons), 6.6–8.0 (8H,m, aromatic and furyl protons); U.V. spectrum (95% ethanol), λ$_{max}$ 272 nm (ε=25,690). Paper chromatography showed a zone at R$_f$=0.50.

EXAMPLE 54

Sodium 7-[D-α-(3-crotonoyl-3-methylureido)-phenylacetamido]-3-(2-methyl-1,3,4-thiadiazol-5-ylthio)methylceph-3-em-4-carboxylate From N-chlorocarbonyl-N-methyl crotonamide and 7-(D-α-aminophenylacetamido)-3-(2-methyl-1,3,4-thiadiazol-5-ylthio)methylceph-3-em-4-carboxylic acid t.f.a. salt in 38.8% yield; N.M.R. spectrum [(CD$_3$)$_2$SO+D$_2$O], δ=1.8–2.1 (3H,m, crotonyl —CH$_3$), 2.70 (3H,s, thiadiazole —CH$_3$), 3.25 (3H,s, >N—CH$_3$), 3.5–3.7 (2H,m, C$_2$ methylene protons), 4.3–4.5 (2H,m, —CH$_2$S—), 4.9–5.1 (1H,m, C$_6$ proton), 5.5–5.8 (2H,m, C$_7$ and α-protons), 6.6–7.1 (2H,m, olefinic protons), 7.40 (5H,s, aromatic protons); U.V. spectrum (95% ethanol), λ$_{max}$ 273 nm (ε=14,510), Paper chromatography showed a zone at R$_f$=0.65.

EXAMPLE 55

Sodium 7-[D-α-(3-crotonoyl-3-methylureido)-phenylacetamido]-3-(1-methyl-1H-tetrazol-5-ylthio)methylceph-3-em-4-carboxylate From N-chlorocarbonyl-N-methylcrotonamide and 7-(D-α-aminophenylacetamido)-3-(1-methyl-1H-tetrazol-5-ylthio)methylceph-3-em-4-carboxylic acid t.f.a. salt in 30.6% yield; N.M.R. spectrum [(CD$_3$)$_2$SO+D$_2$O], δ=1.9-2.1 (3H,m, crotonyl —CH$_3$), 3.23 (3H,s, >N—CH$_3$), 3.4-3.7 (2H,m, C$_2$ methylene protons), 3.94 (3H,s, tetrazole —CH$_3$), 4.2-4.4 (2H,m, —CH$_2$S—), 4.9-5.1 (1H,m, C$_6$ proton), 5.5-5.8 (2H,m, C$_7$ and α-protons), 6.6-7.1 (2H,m, olefinic protons), 7.39 (5H,s, aromatic protons); U.V. spectrum (95% ethanol), λ$_{max}$ 270 nm (ε=10,010). Paper chromatography showed a zone at R$_f$=0.45.

EXAMPLE 56

Sodium 7-[D-α-[3-(2-chlorobenzoyl)-3-methylureido]-phenylacetamido]-3-(2-methyl-1,3,4-thiadiazol-5-ylthio)methylceph-3-em-4-carboxylate From N-chlorocarbonyl-N-methyl-2-chlorobenzamide and 7-(D-α-aminophenylacetamido)-3-(2-methyl-1,3,4-thiadiazol-5-ylthio)methylceph-3-em-4-carboxylic acid t.f.a. salt in 31.8% yield; N.M.R. spectrum [(CD$_3$)$_2$SO+D$_2$O], δ=2.68 (3H,s, thiadiazole —CH$_3$), 2.98 (3H,s, >N—CH$_3$), 3.3-3.6 (2H,m, C$_2$ methylene protons), 4.3-4.6 (2H,m, —CH$_2$S—), 4.8-5.0 (1H,m, C$_6$ proton), 5.5-5.8 (2H,m, C$_7$ and α-protons), 7.3-7.7 (9H,d, aromatic protons); U.V. spectrum (95% ethanol), λ$_{max}$ 276 nm (ε=11,910). Paper chromatography showed a zone at R$_f$=0.54.

EXAMPLE 57

Sodium 7-[D-α-[3-(2-methylbenzoyl)-3-methylureido]-phenylacetamido]-3-(2-methyl-1,3,4-thiadiazol-5-ylthio)methylceph-3-em-4-carboxylate From N-chlorocarbonyl-N-methyl-2-methylbenzamide and 7-(D-α-aminophenylacetamido)-3-(2-methyl-1,3,4-thiadiazol-5-ylthio)methylceph-3-em-4-carboxylic acid t.f.a. salt in 32.7% yield; N.M.R. spectrum [(CD$_3$)$_2$SO+D$_2$O], δ=2.27 (3H,s, benzoyl —CH$_3$), 2.68 (3H,s, thiadiazole —CH$_3$), 2.97 (3H,s, >N—CH$_3$), 3.3-3.6 (2H,m, C$_2$ methylene protons), 4.4-4.6 (2H,m, —CH$_2$S—), 5.3-5.5 (1H,m, C$_6$ proton), 5.6-5.8 (2H,m, C$_7$ and α-protons), 7.3-7.6 (9H,m, aromatic protons); U.V. spectrum (95% ethanol), λ$_{max}$ 274 nm (ε=12,190). Paper chromatography showed a zone at R$_f$=0.62.

EXAMPLE 58

Sodium 7-[D-α-(3-acetylimidazolidin-2-on-1-ylcarbonylamino)-phenylacetamido]-3-(2-methyl-1,3,4-thiadiazol-5-ylthio)methylceph-3-em-4-carboxylate From 7-(D-α-aminophenylacetamido)-3-(2-methyl-1,3,4-thiadiazol-5-ylthio)methylceph-3-em-4-carboxylic acid t.f.a. salt and 3-acetyl-1-chlorocarbonylimidazolidin-2-one in 74.3% yield; N.M.R. spectrum [(CD$_3$)$_2$SO+D$_2$O], δ=7.43 (5H,s, aromatic protons), 5.7-5.4 (2H,m, C$_7$ and α-protons), 5.1-4.8 (1H,m, C$_6$ proton), 4.7-4.1 (2H,m, —CH$_2$S—), 3.70 (4H,s, imidazolidinone methylene protons), 3.8-3.0 (2H,m, C$_2$ methylene protons), 2.70 (3H,s, thiadiazole —CH$_3$), 2.45 (3H,s, >NCOCH$_3$); U.V. spectrum (95% ethanol), λ$_{max}$ 274.5 nm (ε=10,270). Paper chromatography showed one zone, R$_f$=0.43.

EXAMPLE 59

Sodium 7-[D-α-(3-acetylimidazolidin-2-on-1-ylcarbonylamino)-phenylacetamido]-3-(1-methyl-1H-tetrazol-5-ylthio)methylceph-3-em-4-carboxylate From 7-(D-α-aminophenylacetamido)-3-(1-methyl-1H-tetrazol-5-ylthio) methylceph-3-em-4-carboxylic acid t.f.a. salt and 3-acetyl-1-chlorocarbonylimidazolidin-2-one in 43.5% yield; N.M.R. spectrum [(CD$_3$)$_2$SO+D$_2$O], δ=7.47 (5H,s, aromatic protons), 5.8-5.4 (2H,m, C$_7$ and α-protons), 5.0-4.8 (1H,m, C$_6$ proton), 4.7-4.0 (2H,m, —CH$_2$S—), 3.96 (3H,s, tetrazole —CH$_3$), 3.70 (4H,s, imidazolidinone methylene protons), 3.8-3.1 (2H,m, C$_2$ methylene protons), 2.45 (3H,s, >NCOCH$_3$); U.V. spectrum (95% ethanol), λ$_{max}$ 265 nm (ε=8,400). Paper chromatography showed one zone, R$_f$=0.38.

EXAMPLE 60

Sodium D-α-(imidazolidin-2-on-1-ylcarbonylamino)benzyl cephalosporin

Anhydrous triethylammonium D-α-aminobenzyl cephalosporin in dichloromethane (30 ml) (prepared from the dihydrate (2.2 g., 0.005 M) as described in example 3) was cooled in an ice bath and 1-chlorocarbonylimidazolidin-2-one (0.75 g., 0.005 M) in dichloromethane (10 ml) was added. The solution was stirred at R.T. for three hours then evaporate to dryness in vacuo, the residue dissolved in water (100 ml) and washed with ethyl acetate (2×50 ml). The aqueous solution was covered with ethyl acetate (50 ml) and acidified to pH 1.5 with 1 N hydrochloric acid. The cephalosporin free acid, which precipitated, was collected, washed with water (100 ml) and dried in vacuo. The free acid was suspended in water (25 ml) and adjusted to pH 6.5 with 5 N sodium hydroxide solution then filtered and freeze dried to give the sodium salt. Yield 1.77 g., 68.4%; N.M.R. spectrum [(CD$_3$)$_2$SO+D$_2$O], δ=7.43 (5H,s, aromatic protons), 5.8-5.4 (2H,m, C$_7$ and α-protons), 5.2-4.6 (3H,m, C$_6$ proton and —CH$_2$OCO—), 4.0-3.0 (6H,m, C$_2$ and imidazolidinone methylene protons), 2.00 (3H,s, —OCOCH$_3$); U.V. spectrum (95% ethanol), λ$_{max}$ 264 nm (ε=6,950). Paper chromatography showed one zone, R$_f$=0.27.

EXAMPLE 61

Sodium 7-[D-α-(imidazolidin-2-on-1-ylcarbonylamino)-phenylacetamido]-3-(2-methyl-1,3,4-thiadiazol-5-ylthio)methylceph-3-em-4-carboxylate Prepared from 7-(D-α-aminophenylacetamido)-3-(2-methyl-1,3,4-thiadiazol-5-ylthio)methylceph-3-em-4-carboxylic acid and 1-chlorocarbonylimidazolidin-2-one in 63.5% yield by the method described in Example 60. N.M.R. spectrum [(CD$_3$)$_2$SO+D$_2$O], δ=7.43 (5H,s, aromatic protons), 5.8-5.4 (2H,m, C$_7$ and α-protons), 4.88 [1H,d, (J=5 Hz), C$_6$ proton], 4.8-4.1 (2H,m, —CH$_2$S—), 4.0-3.0 (6H,m, C$_2$ and imidazolidinone methylene protons), 2.69 (3H,s, thiadiazole —CH$_3$); U.V. spectrum (95% ethanol), λ$_{max}$ 275 nm (ε=12,210). Paper chromatography showed one zone, R$_f$=0.38.

EXAMPLE 62

Sodium
7-[D-α-(imidazolidin-2-on-ylcarbonylamino)-phenylacetamido]-3-(1-methyl-tetrazol-5-ylthio)methylceph-3-em-4-carboxylate 7-(D-α-aminophenylacetamido)-3-(1-methyltetrazol-5-ylthio)methylceph-3-em-4-carboxylic acid (1.72., 0.003 M) was acylated with 1-chlorocarbonylimidazolidin-2-one, as in example 60 to give the free acid as a gummy solid. This was dissolved in acetone (30 ml), dried over anhydrous magnesium sulphate and treated with 2 N sodium 2-ethylhexoate in methyl isobutyl ketone. The precipitated sodium salt was collected, washed with anhydrous ether and dried in vacuo. Yield 1.16 g., 65.0%; N.M.R. spectrum [(CD$_3$)$_2$SO+D$_2$O], δ=7.43 (5H,s, aromatic protons), 5.8–5.4 (2H,m, C$_7$ and α-protons), 4.88 [1H,d, (J=5 Hz), C$_6$ proton], 4.7–4.0 (2H,m, —CH$_2$S—), 3.95 (3H,s, tetrazole —CH$_3$), 4.0–3.0 (6H,m, C$_2$ and imidazolidinone methylene protons); U.V. spectrum (95% ethanol), λ$_{max}$ 271 nm (ε=8,600). Paper chromatography showed one zone, R$_f$=0.24.

EXAMPLE 63

Sodium
7-[D-α-(3-cinnamoyl-3-methylureido)-phenylacetamido]-3-(2-methyl-1,3,4-thiadiazol-5-ylthio)methylceph-3-em-4-carboxylate D-α-(3-Cinnamoyl-3-methylureido)benzyl cephalosporin (1.18 g., 0.002 M) and 2-methyl-5-mercapto-1,3,4-thiadiazole (0.53 g., 0.004 M) were dissolved in d.m.f. (25 ml) and pH 6.5 phosphate buffer solution (25 ml), adjusted to pH 6.5 with solid sodium bicarbonate and then heated at 60° for ten hours. The cooled solution was washed with ethyl acetate (2×100 ml) and acidified to pH 1.5 with 1 N hydrochloric acid in the presence of ethyl acetate (50 ml). The organic phase was separated, the aqueous layer was extracted with more ethyl acetate (50 ml) then the combined ethyl acetate extracts were washed with water (2×100 ml) and saturated brine (50 ml), dried over anhydrous magnesium sulphate, treated with 2 N sodium 2-ethylhexoate in methyl isobutyl ketone (0.5 ml) and diluted with anhydrous ether (200 ml). The precipitated sodium salt was washed with anhydrous ether and dried in vacuo. Yield 0.83 g., 60.5%. N.M.R. spectrum [(CD$_3$)$_2$SO+D$_2$O], δ=8.0–7.0 (12H,m, aromatic and olefinic protons), 5.9–5.4 (2H,m, C$_7$ and α-protons), 4.89 [1H,d, (J=5 Hz), C$_6$ proton], 4.8–4.0 (2H,m, —CH$_2$S—), 3.9–3.0 (2H,m, C$_2$ methylene protons), 3.36 (3H,s,>N—CH$_3$), 2.70 (3H, s, thiadiazole —CH$_3$); U.V. spectrum (95% ethanol), λ$_{max}$ 282 nm (ε=27,470). Paper chromatography showed one zone, R$_f$=0.66.

EXAMPLE 64

Sodium
7-[D-α-(3-cinnamoyl-3-methylureido)-phenylacetamido]-3-(2-methyl-1,3,4-oxadiazol-5-ylthio)methylceph-3-em-4-carboxylate Prepared by the method described in example 65 from D-α-(3-cinnamoyl-3-methylureido)-benzyl cephalosporin and 2-methyl-5-mercapto-1,3,4-oxadiazole in 55.2% yield; N.M.R. spectrum [(CD$_3$)$_2$SO+D$_2$O], δ=8.0–7.0 (12H,m, aromatic and olefinic protons), 5.8–5.4 (2H,m, C$_7$ and α-protons), 4.88 [1H,d, (J=5 Hz), C$_6$ proton], 4.6–3.9 (2H,m, —CH$_2$S—], 3.8–2.8 (2H,m, C$_2$ methylene protons), 3.33 (3H,s,>N—CH$_3$), 2.48 (3H,s, oxadiazole —CH$_3$); U.V. spectrum (95% ethanol), λ$_{max}$ 280 nm (ε=24,800). Paper chromatography showed one zone R$_f$=0.59.

EXAMPLE 65

Sodium
7-[D-α-(3-cinnamoyl-3-methylureido)-phenylacetamido]-3-(1-methyl-1H-tetrazol-5-ylthio)methylceph-3-em-4-carboxylate Prepared by the method described in example 63 from D-α-(3-cinnamoyl-3-methylureido)benzyl cephalosporin and 5-mercapto-1-methyl-1H-tetrazole in 56.7% yield; N.M.R. spectrum [(CD$_3$)$_2$SO+D$_2$O], δ=8.0–7.0 (12H,m, aromatic protons), 5.8–5.5 (2H,m, C$_7$ and α-protons), 4.92 [1H,d, (J=5 Hz), C$_6$ proton], 4.7–4.0 (2H,m, —CH$_2$S—), 3.97 (3H,s, tetrazole —CH$_3$), 3.8–3.0 (2H,m, C$_2$ methylene protons), 3.34 (3H,s,>N—CH$_3$); U.V. spectrum (95% ethanol), λ$_{max}$ 284 nm (ε=25,075). Paper chromatography showed one zone, R$_f$=0.53.

EXAMPLE 66

Sodium
7-[D-α-(3-cinnamoyl-3-methylureido)-phenylacetamido]-3-(benzoxazol-2-ylthio)methylceph-3-em-4-carboxylate D-α-(3-Cinnamoyl-3-methylureido)benzyl cephalosporin and (1.18 g., 0.002 M) 2-mercaptobenzoxazole (0.60 g., 0.002 M) in formamide (20 ml) and water (25 ml) were adjusted to pH 7.0 with solid sodium bicarbonate then heated at 60° for ten hours. The cooled solution was washed with ethyl acetate (2×100 ml) filtered, covered with ethyl acetate (100 ml) and acidified to pH 1.5 with 1 N hydrochloric acid. The ethyl acetate was separated, the aqueous layer extracted with ethyl acetate (100 ml) and the organic extracts combined, washed with water (2×100 ml) and brine (50 ml) then dried over anhydrous magnesium sulphate, treated with 2 N sodium 2-ethylhexoate in methyl isobutyl ketone (0.7 ml) and diluted with ether (200 ml). The precipitated sodium salt was collected, washed with ether, dried in vacuo, dissolved in water (50 ml), acidified to pH 1.5 with 1 N hydrochloric acid and the precipitated free acid collected. This was dissolved in ethyl acetate (25 ml), filtered, diluted with ether (25 ml), filtered then evaporated to dryness in vacuo and the residue triturated with ether to give an off white solid (0.21 g.,), which was dissolved in acetone (3 ml), treated with 2 N sodium 2-ethylhexoate in methyl isobutyl ketone (0.31 ml) and diluted with ether (25 ml) to precipitate the sodium salt. This was collected and dried in vacuo 0.16 g., 12% yield; N.M.R. [(CD$_3$)$_2$SO+D$_2$O], δ=8.0–6.9 (16H,m, aromatic and olefinic protons), 5.8–5.5 (2H,m, C$_7$ and α-protons), 5.0–4.8 (1H,m, C$_6$ proton), 4.8–4.0 (2H,m, —CH$_2$S—), 3.8–3.0 (2H,m, C$_2$ methylene protons). 3.34 (3H,m,>N—CH$_3$), U.V. spectrum (95% ethanol), λ$_{max}$ 290 nm (ε=33,050). Paper chromatography showed a zone at R$_f$=0.80.

EXAMPLE 67

Disodium 7-[D-α-(3-cinnamoyl-3-methylureido)-phenylacetamido]-3-(4-sulphophenylthio)methylceph-3-em-4-carboxylate D-α-(3-Cinnamoyl-3-methylureido)benzyl cephalosporin (1.18 g., 0.002 M) and 4-mercaptobenzenesulphonic acid (0.42 g., 0.002 M) in water (10 ml) and d.m.f. (15 ml) were adjusted to pH 6.5 with solid sodium bicarbonate and heated at 60° for eight hours. The solution was evaporated to dryness in vacuo at R.T. and the residue was dissolved in water (100 ml), acidified to pH 1.5 with 'Amberlite' resin IR-120(H), washed with ethyl acetate (2×50 ml) and extracted with n-butanol (2×50 ml). The butanol was removed in vacuo to leave a solid which was triturated with ether and collected, 0.83 g; N.M.R. spectrum [$(CD_3)_2SO + D_2O$], $\delta = 8.0$–7.0 (16H,m, aromatic and olefinic protons), 5.9–5.5 (2H,m, $C_7$ and α-protons), 5.2–4.9 (1H,m, $C_6$ proton), 4.8–4.0 (2H,m, —$CH_2S$—), 3.9–3.0 (2H,m, $C_2$ methylene protons), 3.33 (3H,m, >N—$CH_3$). The solid was dissolved in water, adjusted to pH 6.5 with 1 N sodium hydroxide solution, washed with n-butanol and freeze dried to give the disodium salt, 0.66., 41.8% yield; U.V. spectrum ($H_2O$), $\lambda_{max}$ 275 nm ($\epsilon = 8,040$). Paper chromatography showed a zone at $R_f = 0.35$.

EXAMPLE 68

Disodium 7-[D-α-(3-Cinnamoyl-3-methylureido)-phenylacetamido]-3-sulphomethylceph-3-em-4-carboxylate Sodium D-α-(3-Cinnamoyl-3-methylureido)benzyl cephalosporin (0.05 g., 0.8 m. mole) was dissolved in warm formamide (8 ml). Sodium sulphite (0.15 g., 1.2 m.moles) in water (12 ml) was added, and sufficient $SO_2$ gas passed in to give pH 7.0. The mixture was heated at 60° for 5 hours. If necessary, the pH was adjusted during this period by the addition of $SO_2$ or 5 N sodium hydroxide solution. The mixture was diluted with water and ice (total 30 ml) and acidified to pH 1.5 with strong acid ion exchange resin 'Amberlite' IR-120(H). The solution was filtered, extracted with ethyl acetate (2×50 ml) and then with n-butanol (2×30 ml). The butanol layers were combined, washed with a little water, then water (30 ml) was added, and the pH adjusted to 7.0 by the cautions addition of 1 N sodium hydroxide solution. The aqueous solution was evaporated as far as possible under reduced pressure, and the residue distilled under high vacuum at 40°. The residual gum was triturated with acetonitrile (5.0 ml), and the solid collected, dissolved in water (10 ml) and n-butanol (20 ml). IR-120 (H) resin was added to pH 1.5, the butanol layer separated, evaporated almost to dryness, reevaporated with a further 2×20 ml portions of n-butanol. The residue was partitioned between water (10 ml) and n-butanol (10 ml), 1.0 N sodium hydroxide solution added to pH 7.0. The aqueous layer was freeze-dried, to 0.20 g., N.M.R. spectrum ($D_2O$) $\delta = 7.2$–7.6 (12H,m, aromatic and olefinic protons), 3.25 (3H,s,>N—$CH_3$); U.V. spectrum ($H_2O$), $\lambda_{max}$ 265 nm ($\epsilon = 6,990$). Paper chromatography showed one zone at $R_f = 0.10$.

EXAMPLE 69

Sodium D,L-α-(3-cinnamoyl-3-methylureido)thien-2-ylmethyl cephalosporin

D,L-α-(3-Cinnamoyl-3-methylureido)thien-2-ylacetic acid (1.72 g., 0.005 M), N-methylmorpholine (1 drop) and triethylamine (0.71 ml., 0.005 M) in anhydrous acetone (15 ml) were cooled to −10° and treated with ethyl chloroformate (0.48 ml, 0.005 M). The solution was stirred at between −5° and 10° for 20 minutes then a solution of 7-aminocephalosporanic acid (1.36 g., 0.005 M) and triethylamine (0.71 ml) in 50% aqueous acetone (30 ml) cooled to 0° was added. The mixture was stirred at R.T. for two hours, the acetone was removed in vacuo, water (50 ml) added and washed with ethyl acetate (2×50 ml). The aqueous solution was acidified to pH 1.5 with 1 N hydrochloric acid in the presence of ethyl acetate (50 ml) and extracted with a further portion of ethyl acetate (50 ml). The extracts were washed with water (2×100 ml) and brine (50 ml) then dried over anhydrous magnesium sulphate, treated with 2 N sodium 2-ethylhexoate in methyl isobutyl ketone (1.8 ml) and diluted with anhydrous ether (200 ml). The precipitated sodium salt was collected, washed with ether and dried. Yield 1.12 g., 36.1%; N.M.R. spectrum [$(CD_3)_2SO + D_2O$], $\delta = 8.0$–6.7 (10H,m, aromatic, olefinic and thienyl protons), 6.0–5.8 (1H,m, α-proton), 5.7–5.3 (1H,m, $C_7$ proton), 5.2–4.5 (3H,m, $C_6$ proton and —$CH_2OCO$—), 3.8–3.0 (2H,m, $C_2$ methylene protons), 3.33 (3H,s, >N—$CH_3$), 2.01 (3H,m, —O-$COCH_3$); U.V. spectrum (95% ethanol), $\lambda_{max}$ 286 nm ($\epsilon = 21,650$). Paper chromatography showed one zone, $R_f = 0.53$.

EXAMPLE 70

Sodium 7-[D,L-α-(3-cinnamoyl-3-methylureido)thien-2-ylacetamido]-3-(1-methyl-1H-tetrazol-5-ylthio)methylceph-3-em-4-carboxylate Prepared from 7-amino-3-(1-methyl-1H-tetrazol-5-ylthio)-methylceph-3-em-4-carboxylic acid and D,L-α-(3-cinnamoyl-3-methylureido)thien-2-ylacetic acid by the method described in example 69 in 34.0% yield; N.M.R. spectrum [$(CD_3)_2SO + D_2O$], $\delta = 8.0$–6.8 (10H,m, aromatic, olefinic and thienyl protons), 6.0–5.7 (1H,m, α-proton), 5.7–5.3 (1H,m, $C_7$ proton), 5.1–4.8 (1H,m, $C_6$ proton), 4.6–4.0 (2H,m, —$CH_2S$—), 2.93 (3H,s,tetrazole —$CH_3$), 3.8–3.1 (2H,m, $C_2$ methylene protons), 3.34 (3H,s,>N—$CH_3$); U.V. spectrum (95% ethanol), $\lambda_{max}$ 285 nm ($\epsilon = 25,190$). Paper chromatography showed one zone, $R_f = 0.52$.

EXAMPLE 71

Sodium D-α-(3-cinnamoyl-3-methylureido)benzyl cephalosporin

D-α-(3-Cinnamoyl-3-methylureido)phenylacetic acid (1.69 g., 0.005 M) and 1-hydroxybenztriazole monohydrate (0.77 g., 0.005 M) in t.h.f. (10 ml) were cooled in an ice bath then treated with dicyclohexylcarbodiimide (13 g., 0.005 M). The mixture was left at 5° overnight, then acetic acid (4 drops) was added, the mixture stirred at R.T. for 15 minutes after which time the dicyclohexylurea was filtered off and washed with tetrahydrofuran (5 ml). The filtrate was added to 7-aminocephalosporanic acid (1.36 g., 0.005 M) in 50% aqueous t.h.f. (30 ml) which had been adjusted to pH 6.5 with N-methyl-morpholine. The solution was stirred at pH 6.5-7.0 for three hours then the t.h.f. was removed in vacuo and the residue diluted with water (50 ml). This aqueous solution was worked up to give the sodium salt as described in example 71. Yield 1.21 g., 39.4%; N.M.R. [(CD$_3$)$_2$SO+D$_2$O], δ=8.0-7.0 (12H,m, aromatic and olefinic protons), 5.8-5.5 (2H,m, C$_7$ and α-protons), 5.2-4.6 (3H,m, C$_6$ proton and —CH$_2$OCO—), 3.8-2.9 (2H,m, C$_2$ methylene protons), 3.33 (3H,s,>N—CH$_3$), 2.02 (3H,s, —OCOCH$_3$); U.V. spectrum (95% ethanol), λ$_{max}$ 286 nm (ε=21,010). Paper chromatography showed one zone R$_f$=0.54.

We claim:

1. A compound of the formula:

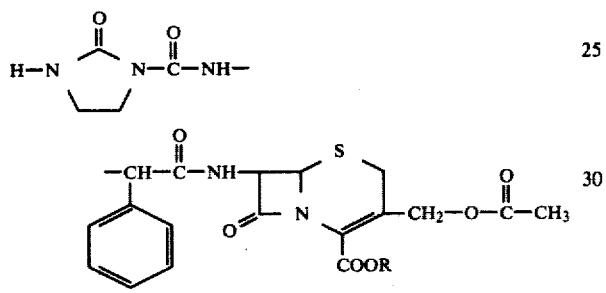

wherein R is hydrogen or sodium.

2. A compound of the formula:

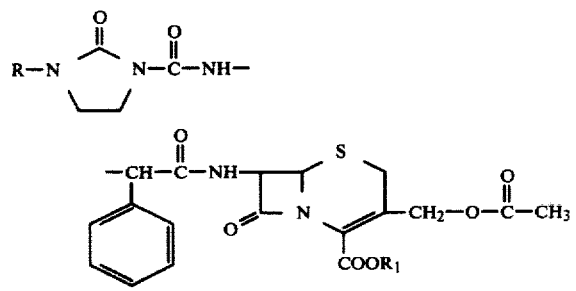

wherein R is

or CH$_3$SO$_2$— and R$_1$ is hydrogen or sodium.

3. The compound of the formula

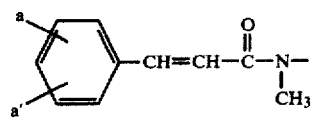

-continued

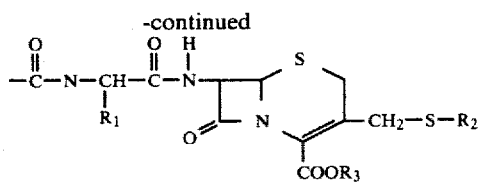

wherein
a and a' are independently hydrogen, halogen or nitro;
R$_1$ is phenyl, monohydroxyphenyl, mono- or dihalophenyl, monohydroxy substituted mono- or dihalophenyl or thienyl;
R$_2$ is

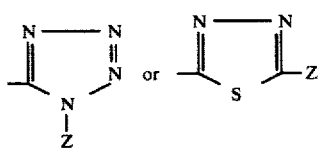

wherein
Z is methyl;
R$_3$ is hydrogen, phthalidyl or an acyloxymethyl group of the formula

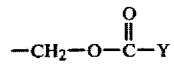

wherein
Y is C$_1$–C$_4$ alkyl; and when
R$_3$ is hydrogen, the pharmaceutically acceptable, nontoxic salts thereof.

4. The compound of claim 3 wherein R$_1$ is phenyl, monohydroxphenyl, monohydroxy substituted mono- or dihalophenyl or thienyl; R$_3$ is hydrogen or the pharmaceutically acceptable, nontoxic salts thereof.

5. The compound of claim 3, said compound being 7-[α-(3-cinnamoyl-3-methyl-1-ureido)-2-phenylacetamido]-3-(1-methyl-1H-tetrazole-5-ylthiomethyl)-3-cephem-4-carboxylic acid.

6. The compound sodium 7-[D-α-(3-cinnamoyl-3-methylureido)phenylacetamido]-3-(2-methyl-1,3,4-thiadiazol-5-ylthio)methylceph-3-em-4-carboxylate.

7. The compound sodium 7-[D-α-(3-cinnamoyl-3-methylureido)phenylacetamido]-3-(1-methyl-1H-tetrazol-5-ylthio)methylceph-3-em-4-carboxylate.

8. The compound sodium 7-[D-α-(3-cinnamoyl-3-methylureido)phenylacetamido]-3-(1H-1,2,4-triazol-3-ylthio)methylceph-3-em-4-carboxylate.

9. The compound sodium 7-[D-α-(3-cinnamoyl-3-methylureido)phenylacetamido]-3-(2-methyl-1,3,4-oxadiazol-5-ylthio)methylceph-3-em-4-carboxylate.

10. The compound sodium 7-[D-α-(3-cinnamoyl-3-methylureido)phenylacetamido]-3-(benzoxazol-2-ylthio)methylceph-3-em-4-carboxylate.

11. The compound disodium 7-[D-α-(3-cinnamoyl-3-methylureido)phenylacetamido]-3-(4-sulphophenylthio)methylceph-3-em-4-carboxylate.

12. The compound disodium 7-[D-α-(3-cinnamoyl-3-methylureido)phenylacetamido]-3-sulphomethylceph-3-em-4-carboxylate.

13. The compound sodium 7-[D,L-α-(3-cinnamoyl-3-methylureido)thien-2-ylacetamido]-3-(1-methyl-1H-tetrazol-5-ylthio)methylceph-3-em-4-carboxylate.

* * * * *